United States Patent
Davies et al.

(10) Patent No.: US 10,207,984 B2
(45) Date of Patent: Feb. 19, 2019

(54) CYCLOPROPYL DERIVATIVES AND METHODS OF USE

(71) Applicants: Emory University, Atlanta, GA (US); Wake Forest University Health Sciences, Winston-Salem, NC (US)

(72) Inventors: Huw M. L. Davies, Duluth, GA (US); Spandan Chennamadhavuni, Natick, MA (US); Thomas J. Martin, Walkertown, NC (US); Steven R. Childers, Winston-Salem, NC (US)

(73) Assignees: Emory University, Atlanta, GA (US); Wake Forest University Health Services, Winston-Salem, NC (US)

( * ) Notice: Subject to any disclaimer, the term of this patent is extended or adjusted under 35 U.S.C. 154(b) by 0 days.

(21) Appl. No.: 15/145,323

(22) Filed: May 3, 2016

(65) Prior Publication Data
US 2016/0244403 A1     Aug. 25, 2016

Related U.S. Application Data

(63) Continuation of application No. 14/110,660, filed as application No. PCT/US2012/033423 on Apr. 13, 2012, now abandoned.

(51) Int. Cl.
*C07C 229/46*     (2006.01)
*A61K 31/195*     (2006.01)
(Continued)

(52) U.S. Cl.
CPC .......... *C07C 229/46* (2013.01); *A61K 31/195* (2013.01); *A61K 31/216* (2013.01);
(Continued)

(58) Field of Classification Search
None
See application file for complete search history.

(56) References Cited

U.S. PATENT DOCUMENTS 4,478,836 A     10/1984    Mouzin
4,567,288 A     1/1986     Cousse
(Continued)

FOREIGN PATENT DOCUMENTS

FR     2302994     3/1975
FR     2581060     4/1985
(Continued)

OTHER PUBLICATIONS

Knittel et al (Foye's Principles of Medicinal Chemistry, 5th Edition, 2002; 37-67.*
(Continued)

*Primary Examiner* — Marcos L Sznaidman
*Assistant Examiner* — Rayna Rodriguez
(74) *Attorney, Agent, or Firm* — Emory Patent Group

(57) ABSTRACT

The disclosure relates to cyclopropyl derivatives and methods of use. In some embodiments, the disclosure relates to methods of managing medical disorders with pharmaceutical compositions disclosed herein administered to subject in need thereof. In certain embodiments, the disclosure relates to methods of managing mental disorders, mood disorders, pain, and fibromyalgia and related conditions with pharmaceutical compositions disclosed herein.

4 Claims, 4 Drawing Sheets

| Entry | Ar | % Yield (A) | % Yield (B) | % Yield (C) |
|-------|----|-----|-----|-----|
| a | Phenyl | 93 | 86 | 63 |
| b | 4-Bromo Phenyl | 94 | 93 | 56 |
| c | Biphenyl | 84 | 83 | 78 |
| d | 2-Napthyl | 90 | 53 | 60 |
| e | 3,4 Dichloro Phenyl | 95 | 88 | 57 |
| f | 2-Chloro Phenyl | 97 | 70 | 60 |
| g | 3,4 Dimethyl Phenyl | 92 | | 56 (2 Steps) |

Related U.S. Application Data

(60) Provisional application No. 61/477,878, filed on Apr. 21, 2011.

(51) Int. Cl.
| | | |
|---|---|---|
| *A61K 45/06* | (2006.01) | |
| *C07C 227/16* | (2006.01) | |
| *C07C 67/313* | (2006.01) | |
| *C07C 69/757* | (2006.01) | |
| *C07C 227/04* | (2006.01) | |
| *A61K 31/216* | (2006.01) | |

(52) U.S. Cl.
CPC ............ *A61K 45/06* (2013.01); *C07C 67/313* (2013.01); *C07C 69/757* (2013.01); *C07C 227/04* (2013.01); *C07C 227/16* (2013.01); *C07C 2601/02* (2017.05)

(56) References Cited

U.S. PATENT DOCUMENTS

| | | | |
|---|---|---|---|
| 5,034,541 | A | 7/1991 | Bigg |
| 7,030,267 | B2 | 4/2006 | Schwarz |
| 2004/0259953 | A1 | 12/2004 | Deregnaucourt |
| 2008/0033014 | A1* | 2/2008 | Griebel ............... A61K 31/135 514/329 |

FOREIGN PATENT DOCUMENTS

| | | |
|---|---|---|
| FR | 2640970 | 12/1988 |
| RU | 2312853 | 1/2007 |
| SU | 1443797 | 4/1986 |
| WO | 9522521 | 8/1995 |
| WO | 9804517 | 2/1998 |
| WO | 0064583 | 11/2000 |
| WO | 2004039320 | 5/2004 |
| WO | 2005016884 | 2/2005 |
| WO | 2005117872 | 12/2005 |

OTHER PUBLICATIONS

Clauw et al (Clinical Therapeutics, 2008; 30(11):1988-2004).*
Bonnaud et al. 1-Aryl-2-(aminomethyl)cyclopropanecarboxylic Acid Derivatives. A New Series of Potential Antidepressants, J. Med. Chem. 1987,30, 318-325.
Li et al. Excretion and Metabolism of Milnacipran in Humans after Oral Administration of Milnacipran Hydrochloride, Drug Metabolism and Disposition, 40:1723-1735, 2012.
Milnacipran, Savella® (milnacipran HCl), Tablets Label, Revised: Nov. 2011.
Paulini et al. Preparation of Novel Lipophilic GABA Analogues Containing Cydopropane Rings via Cydopropanation of N-Silylated Unsaturated Amines, Journal fur praktische Chemie Chemiker-Zeitung, 337 (1995) 55-59.
Roggen et al. Synthesis of enantiomerically pure milnacipran analogs and inhibition of dopamine, serotonin, and norepinephrine transporters, Bioorganic & Medicinal Chemistry Letters 17 (2007) 2834-2837.
Shuto et al. (±)-(Z)-2-(Aminomethyl)-1-phenylcyclopropanecarboxamide Derivatives as a New Prototype of NMDA Receptor Antagonists, J. Med. Chem. 1995, 38, 2964-2968.
Sisay et al. Structural Interpretation of Activity Cliffs Revealed by Systematic Analysis of Structure-Activity Relationships in Analog Series, J. Chem. Inf. Model. 2009, 49, 2179-2189.
Stumpfe et al. Exploring Activity Cliffs in Medicinal Chemistry, J. Med. Chem. 2012, 55, 2932-2942.
Turner et al. Screening Methods in Pharmacology 1st Edition, Introduction, 1971.
Extended European Search Report for EP Application No. 12774505.7 dated Sep. 3, 2014.

* cited by examiner

| Entry | Ar | % Yield (A) | % Yield (B) | % Yield (C) |
|---|---|---|---|---|
| a | Phenyl | 93 | 86 | 63 |
| b | 4-Bromo Phenyl | 94 | 93 | 56 |
| c | Biphenyl | 84 | 83 | 78 |
| d | 2-Napthyl | 90 | 53 | 60 |
| e | 3,4 Dichloro Phenyl | 95 | 88 | 57 |
| f | 2-Chloro Phenyl | 97 | 70 | 60 |
| g | 3,4 Dimethyl Phenyl | 92 | | 56 (2 Steps) |

CYCLOPROPYL DERIVATIVES AND METHODS OF USE

CROSS-REFERENCE TO RELATED APPLICATIONS

This application is a continuation of U.S. application Ser. No. 14/110,660 filed Oct. 8, 2013, which is the National Stage of International Application No. PCT/US2012/033423 filed Apr. 13, 2012, which claims the benefit of U.S. Provisional Application No. 61/477,848 filed Apr. 21, 2011. The entirety of each of these applications is hereby incorporated by reference for all purposes.

STATEMENT REGARDING FEDERALLY SPONSORED RESEARCH OR DEVELOPMENT

This invention was made with government support under Grants R01 DA023224 and R01 DA022599 awarded by the National Institutes of Health. The government has certain rights in the invention.

FIELD

The disclosure relates to cyclopropyl derivatives and methods of use. In some embodiments, the disclosure relates to methods of managing medical disorders with pharmaceutical compositions disclosed herein administered to subject in need thereof. In certain embodiments, the disclosure relates to methods of managing mental disorders, mood disorders, pain, fibromyalgia, and related conditions with pharmaceutical compositions disclosed herein.

BACKGROUND

Fibromyalgia is a medical disorder characterized by chronic widespread pain and allodynia. Fibromyalgia is frequently comorbid with psychiatric conditions such as depression, anxiety, and stress-related disorders. Currently, there is no cure for fibromyalgia. Medical therapies with anti-depressants have demonstrated the ability to reduce symptoms. Milnacipran is a cyclopropylamide and a selective norepinephrine and serotonin reuptake inhibitor (SNRI) approved by the FDA for the management of fibromyalgia. A significant percentage of patients discontinue taking milnacipran due to adverse events such as nausea, palpitations, depression, increased heart rate, constipation, and headaches. Other adverse events reported when taking milnacipran include increases in heart rate and blood pressure, serotonin syndrome, seizures, hepatotoxicity, hyponatremia, abnormal bleeding, activation of mania and dysuria. Thus, there is a need to identify improved therapies.

Bonnarud et al., J Med Chem, 1987, 30, 318-325 disclose cyclopropane carbocylic acid derivatives. See also U.S. Pat. No. 4,567,288 and U.S. Published Application No. 2008/0051604. The authors report uses as antidepressants and for the treatment of pain. Certain cyclopropyl derivatives are also disclosed in Davies & Denton, Chem. Soc. Rev., 2009, 38, 3061-3071; Pelphrey et al., Chem. Sci., 2010, 1, 254-257, Davies et al., Tetrahedron Letters, (1996) 37(24), 4133-4136, Denton & Davies, Organic Letters, (2009) 11(4), 787-790. See also U.S. Pat. No. 7,385,064.

SUMMARY

This disclosure relates to cyclopropyl derivatives and methods of use. In some embodiments, the disclosure relates to methods of managing, treating, or preventing medical disorders with pharmaceutical compositions disclosed herein administered in an effective amount to subject in need thereof. In certain embodiments, the disclosure relates to methods of managing mental disorders, mood disorders, pain, and fibromyalgia and related conditions with pharmaceutical compositions disclosed herein. In certain embodiments, the disclosure relates to compounds comprising the following formula I:

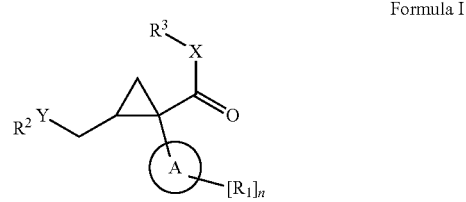

Formula I and salts, prodrugs, or esters thereof wherein,
A ring is a carbocyclyl, aryl, or heterocyclyl;
n is 0, 1, 2, 3, 4, or 5;
X and Y are each the same or different O, S, $NR^4$;
$R^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;
$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;
$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;
$R^4$ is hydrogen, alkyl, hydroxy, amino, formyl, carbocyclyl, aryl, or heterocyclyl, wherein $R^4$ is optionally substituted with one or more, the same or different, $R^5$;
$R^5$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and
$R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to a composition comprising a compound disclosed herein in greater than 60%, 70%, 80%, 90%, 95%, 98%, 99%, or 99.5% diastereomeric excess.

In certain embodiments, the disclosure relates to an isolated composition of a compound disclosed herein in substantially pure form.

In certain embodiments, the disclosure relates to a pharmaceutical composition comprising a compound disclosed herein or pharmaceutically acceptable salt or prodrug thereof.

In certain embodiments, the disclosure relates to a pharmaceutical composition disclosed herein further comprising a second therapeutic agent.

In certain embodiments, the disclosure relates to a method of treating or preventing a mental or neurological disorder comprising administering an effective amount of a pharmaceutical composition disclosed herein to a subject diagnosed with, exhibiting symptoms of, or at risk for a mental or neurological disorder.

In certain embodiments, the disclosure relates to methods of preparing compounds disclosed herein comprising mixing the starting material and reagents under conditions such that the products are formed.

DETAILED DISCUSSION

Figure 1:
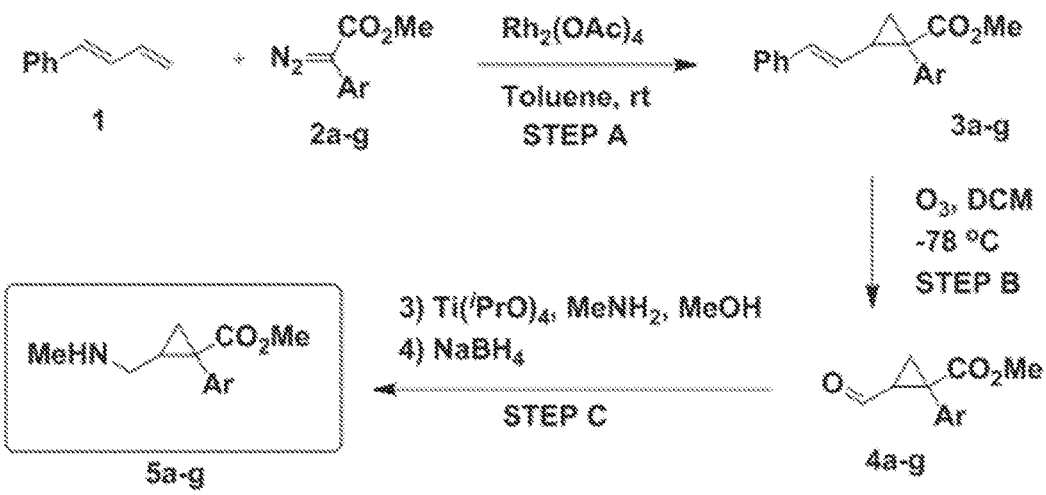
FIG. 1 shows a scheme illustrating the synthesis of racemic cyclopropane amines.
Figure 2:
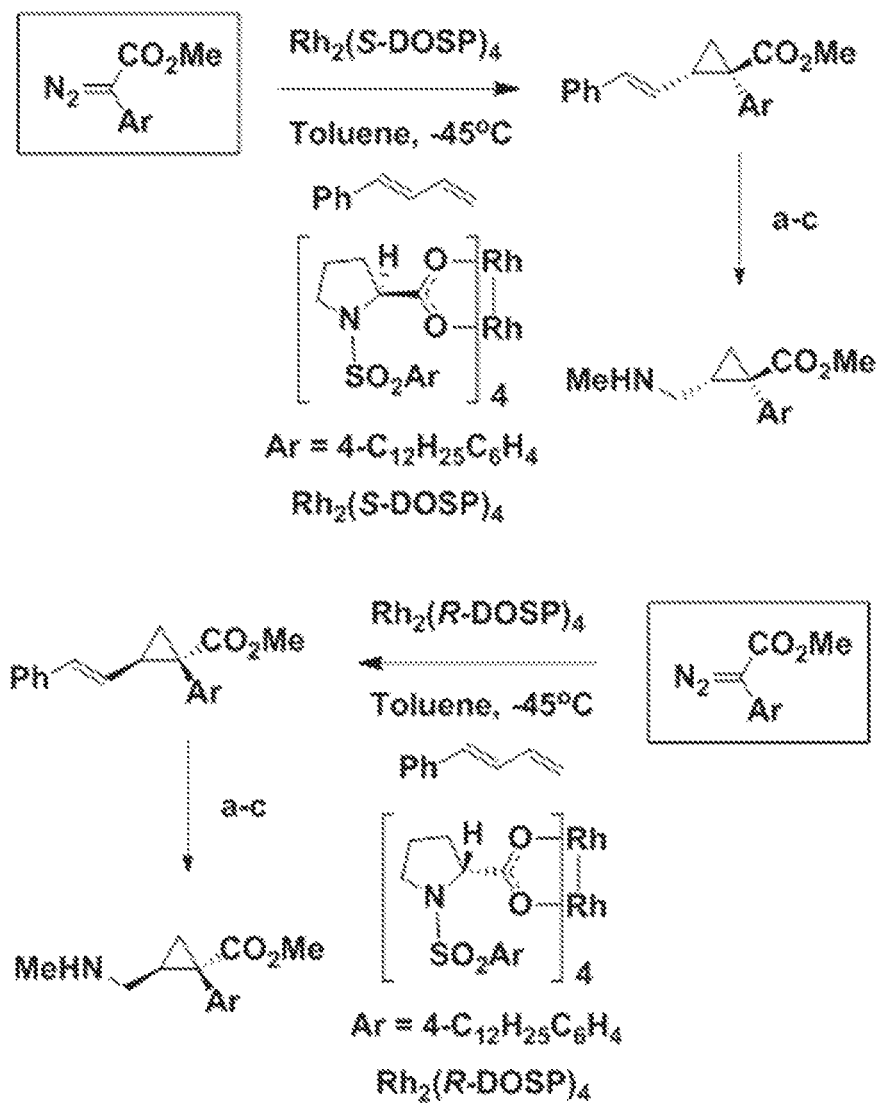
FIG. 2 shows a scheme illustration synthesis of certain diastereomers of cyclopropane amines. a) $O_3$, DCM, $-78°$ C. b) Ti($^i$PrO)$_4$, MeNH$_2$, MeOH, rt c) NaBH$_4$, rt.

The disclosure relates to cyclopropyl derivatives and methods of use. In some embodiments, the disclosure relates to methods of managing medical disorders with pharmaceutical compositions disclosed herein administered to subject in need thereof. In certain embodiments, the disclosure relates to methods of managing mental disorders, mood disorders, pain, and fibromyalgia and related conditions with pharmaceutical compositions disclosed herein.

Compounds

In certain embodiments, the disclosure relates to compounds comprising the following formula I:

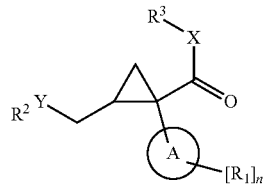

Formula I and salts, prodrugs, or esters thereof wherein,

A ring is a carbocyclyl, aryl, or heterocyclyl;

n is 0, 1, 2, 3, 4, or 5;

X and Y are each the same or different O, S, NR$^4$;

R$^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^5$;

R$^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^2$ is optionally substituted with one or more, the same or different, R$^5$;

R$^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^5$;

R$^4$ is hydrogen, alkyl, hydroxy, amino, formyl, carbocyclyl, aryl, or heterocyclyl, wherein R4 is optionally substituted with one or more, the same or different, R$^5$;

R$^5$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^6$; and R$^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the A ring is aryl or heteroaryl;

n is 0, 1, 2, or 3;

X is oxygen;

Y is NR$^4$;

R$^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^5$;

R$^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;

$R^3$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, hydroxy, amino, formyl, carbocyclyl, aryl, or heterocyclyl, wherein R4 is optionally substituted with one or more, the same or different, $R^5$;

$R^5$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and $R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the A ring is aryl or heteroaryl;
n is 0, 1, 2, or 3;
X is oxygen;
Y is $NR^4$ wherein $R^2$ and $R^4$ and the atoms to which they are attached form a heterocyclyl optionally substituted with one or more, the same or different $R^5$;

$R^1$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^2$ is hydrogen or alkyl;
$R^3$ is hydrogen or alkyl;
$R^4$ is hydrogen or alkyl;

$R^5$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; and $R^6$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the A ring is aryl;
n is 0, 1, 2, or 3;
X is oxygen;
Y is NH;

$R^1$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^2$ is hydrogen or alkyl;
$R^3$ is hydrogen or alkyl;

$R^5$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, or N-methyl-N-ethylsulfamoyl.

In certain embodiments, the disclosure relates to a compound of formula I, wherein formula I is formula IA, IB, IC, or ID wherein:

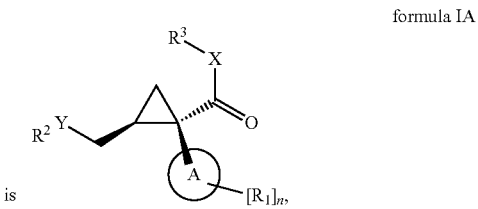

formula IA

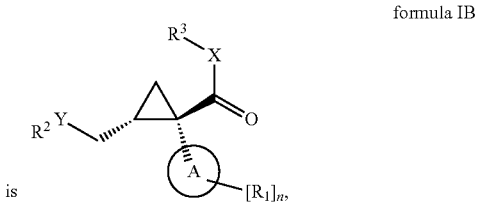

formula IB

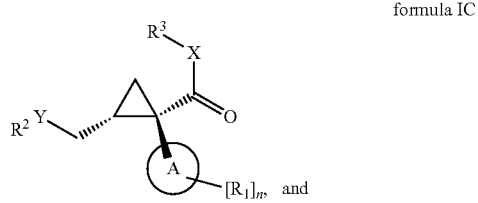

formula IC

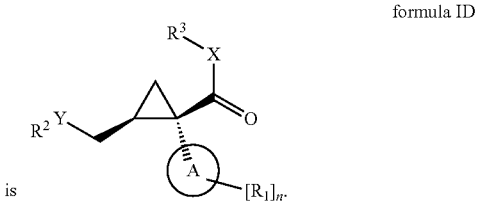

formula ID

In certain embodiments, the A ring is aryl or heteroaryl.
In certain embodiments, the A ring is aryl or heteroaryl and X is oxygen or $NR^4$.
In certain embodiments, the A ring is aryl or heteroaryl, $R^3$ is hydrogen or $C_{1-4}$alkyl and X is oxygen or $NR^4$.
In certain embodiments, the A ring is aryl or heteroaryl, $R^2$ is hydrogen or $C_{1-4}$alkyl, Y is $NR^4$ or oxygen, and X is oxygen or $NR^4$.
In certain embodiments, the A ring is aryl or heteroaryl, $R^1$ is a hydrogen, halogen, or alkoxy, X is oxygen, Y is $NR^4$, and $R^2$ is hydrogen or $C_{1-4}$alkyl.

In certain embodiments, the A ring is aryl or heteroaryl, Y is $NR^4$ or oxygen, and X is oxygen or $NR^4$.

In certain embodiments, the A ring is phenyl, napthyl or biphenyl.

In certain embodiments, the A ring is phenyl, napthyl or biphenyl and X is oxygen or $NR^4$.

In certain embodiments, the A ring is phenyl, napthyl or biphenyl, $R^3$ is hydrogen or $C_{1-4}$alkyl and X is oxygen or $NR^4$.

In certain embodiments, the A ring is phenyl, napthyl or biphenyl, Y is $NR^4$ or oxygen and X is oxygen or $NR^4$.

In certain embodiments, the A ring is phenyl, napthyl or biphenyl, $R^2$ is hydrogen or $C_{1-4}$alkyl, Y is $NR^4$, and X is oxygen.

In certain embodiments, the A ring is phenyl, napthyl or biphenyl, $R^1$ is a hydrogen, halogen, or alkoxy, X is oxygen, and $R^2$ is hydrogen or $C_{1-4}$alkyl.

In certain embodiments, X is oxygen.

In certain embodiments, X is $NR^4$, wherein $R^4$ is hydrogen or $C_{1-4}$alkyl.

In certain embodiments, Y is $NR^4$, wherein $R^4$ is hydrogen or $C_{1-4}$alkyl.

In certain embodiments, $R^3$ is hydrogen or $C_{1-4}$alkyl.

In certain embodiments, $R^3$ is methyl or ethyl.

In certain embodiments, $R^2$ is hydrogen or $C_{1-4}$alkyl.

In certain embodiments, $R^2$ is methyl or ethyl.

In certain embodiments, $R^1$ is a hydrogen, halogen, or $C_{1-4}$alkoxy.

In certain embodiments, $R^1$ is methoxy or ethoxy.

In certain embodiments, n is 0, 1, 2, or 3;

In certain embodiments, n is 0, 1 or 2.

In certain embodiments, n is 1 or 2.

In certain embodiments, the disclosure relates to a compound of formula IA, wherein the A ring is aryl. In certain embodiments, the A ring is phenyl. In certain embodiments, the A ring is napthyl. In certain embodiments, the A ring is biphenyl. In certain embodiments, the A ring is aryl and X is oxygen or $NR^4$. In certain embodiments, the A ring is aryl, $R^3$ is hydrogen or $C_{1-4}$alkyl and X is oxygen. In certain embodiments, the A ring is aryl, Y is $NR^4$ or oxygen, X is oxygen. In certain embodiments, the A ring is aryl, $R_2$ is hydrogen or $C_{1-4}$alkyl, Y is $NR^4$, and X is oxygen. In certain embodiments, the A ring is aryl, $R^1$ is a hydrogen, halogen, or alkoxy, X is oxygen, and $R^2$ is hydrogen or $C_{1-4}$alkyl. In certain embodiment, $R^4$ is $C_{1-4}$alkyl.

In certain embodiments, the disclosure relates to a compound of formula IB, wherein the A ring is aryl. In certain embodiments, the A ring is phenyl. In certain embodiments, the A ring is napthyl. In certain embodiments, the A ring is biphenyl. In certain embodiments, the A ring is aryl and X is oxygen or $NR^4$. In certain embodiments, the A ring is aryl, $R^3$ is hydrogen or $C_{1-4}$alkyl and X is oxygen. In certain embodiments, the A ring is aryl, Y is $NR^4$ or oxygen, and X is oxygen. In certain embodiments, the A ring is aryl, $R^2$ is hydrogen or $C_{1-4}$alkyl, Y is $NR^4$, and X is oxygen. In certain embodiments, the A ring is aryl, $R^1$ is a hydrogen, halogen, or alkoxy, X is oxygen, and $R^2$ is hydrogen or $C_{1-4}$alkyl. In certain embodiment, $R^4$ is $C_{1-4}$alkyl.

In certain embodiments, the disclosure relates to compositions comprising a compound of formula IA, in greater than 60%, 70%, 80%, 90%, 95%, or 98% diastereomeric excess wherein the A ring is aryl, X is oxygen, Y is $NR^4$, $R^3$ is $C_{1-4}$alkyl, $R^2$ is hydrogen or $C_{1-4}$alkyl, $R^1$ is a hydrogen, halogen, or alkoxy, and n is 1 or 2. In certain embodiments, the A ring is phenyl. In certain embodiments, A ring is phenyl substituted with one or more halogens. In certain embodiments substituted at the 3 and 4 position of the phenyl ring. In certain embodiments, the A ring is napthyl. In certain embodiments, the A ring is biphenyl. In certain embodiments, $R^2$ is $C_{1-4}$alkyl. In certain embodiment, $R^4$ is $C_{1-4}$alkyl.

In certain embodiments, the disclosure relates to a composition comprising a compound of formula IB, in greater than 60%, 70%, 80%, 90%, 95%, or 98% diastereomeric excess wherein the A ring is aryl, X is oxygen, Y is $NR^4$, $R^3$ is $C_{1-4}$alkyl, $R^2$ is hydrogen or $C_{1-4}$alkyl, $R^1$ is a hydrogen, halogen, or alkoxy, and n is 1 or 2. In certain embodiment, $R^4$ is $C_{1-4}$alkyl.

In some embodiments, the disclosure relates to a compound selected from:
(1S,2S)-methyl 2-((methylamino)methyl)-1-phenylcyclopropanecarboxylate,
(1S,2S)-2-((methylamino)methyl)-1-phenylcyclopropanecarboxylic acid,
(1S,2S)-methyl 1-(3,4-dichlorophenyl)-2-((methylamino)methyl)cyclopropanecarboxylate,
(1S,2S)-1-(3,4-dichlorophenyl)-2-((methylamino)methyl)cyclopropanecarboxylic acid,
(1S,2S)-methyl 1-(3,4-dibromophenyl)-2-((methylamino)methyl)cyclopropanecarboxylate,
(1S,2S)-1-(3,4-dibromophenyl)-2-((methylamino)methyl)cyclopropanecarboxylic acid,
(1S,2S)-methyl 1-(3,4-dimethoxyphenyl)-2-((methylamino)methyl)cyclopropanecarboxylate,
(1S,2S)-1-(3,4-dimethoxyphenyl)-2-((methylamino)methyl)cyclopropanecarboxylic acid,
(1S,2S)-methyl 1-(2-chlorophenyl)-2-((methylamino)methyl)cyclopropanecarboxylate,
(1S,2S)-1-(2-chlorophenyl)-2-((methylamino)methyl)cyclopropanecarboxylic acid,
(1S,2S)-methyl 1-(4-bromophenyl)-2-((methylamino)methyl)cyclopropanecarboxylate,
(1S,2S)-1-(4-bromophenyl)-2-((methylamino)methyl)cyclopropanecarboxylic acid,
(1S,2S)-methyl 1-(4-methoxyphenyl)-2-((methylamino)methyl)cyclopropanecarboxylate,
(1S,2S)-1-(4-methoxyphenyl)-2-((methylamino)methyl)cyclopropanecarboxylic acid,
(1S,2S)-methyl 1-(2-methoxyphenyl)-2-((methylamino)methyl)cyclopropanecarboxylate,
(1S,2S)-1-(2-methoxyphenyl)-2-((methylamino)methyl)cyclopropanecarboxylic acid,
(1S,2S)-methyl 2-((methylamino)methyl)-1-(naphthalen-2-yl)cyclopropanecarboxylate,
(1S,2S)-2-((methylamino)methyl)-1-(naphthalen-2-yl)cyclopropanecarboxylic acid,
(1S,2S)-methyl 1-([1,1'-biphenyl]-4-yl)-2-((methylamino)methyl)cyclopropanecarboxylate, and
(1S,2S)-1-([1,1'-biphenyl]-4-yl)-2-((methylamino)methyl)cyclopropanecarboxylic acid, or salts thereof.

In certain embodiment the disclosure relates to a compound selected from:
(1R,2R)-methyl 2-((methylamino)methyl)-1-phenylcyclopropanecarboxylate,
(1R,2R)-2-((methylamino)methyl)-1-phenylcyclopropanecarboxylic acid,
(1R,2R)-methyl 1-(3,4-dichlorophenyl)-2-((methylamino)methyl)cyclopropanecarboxylate,
(1R,2R)-1-(3,4-dichlorophenyl)-2-((methylamino)methyl)cyclopropanecarboxylic acid,
(1R,2R)-methyl 1-(3,4-dibromophenyl)-2-((methylamino)methyl)cyclopropanecarboxylate,
(1R,2R)-1-(3,4-dibromophenyl)-2-((methylamino)methyl)cyclopropanecarboxylic acid, (1R,2R)-methyl 1-(3,4-dimethoxyphenyl)-2-((methylamino)methyl)cyclopropanecarboxylate,
(1R,2R)-1-(3,4-dimethoxyphenyl)-2-((methylamino)methyl)cyclopropanecarboxylic acid,
(1R,2R)-methyl 1-(2-chlorophenyl)-2-((methylamino)methyl)cyclopropanecarboxylate,
(1R,2R)-1-(2-chlorophenyl)-2-((methylamino)methyl)cyclopropanecarboxylic acid,
(1R,2R)-methyl 1-(4-bromophenyl)-2-((methylamino)methyl)cyclopropanecarboxylate,
(1R,2R)-1-(4-bromophenyl)-2-((methylamino)methyl)cyclopropanecarboxylic acid,
(1R,2R)-methyl 1-(4-methoxyphenyl)-2-((methylamino)methyl)cyclopropanecarboxylate,
(1R,2R)-1-(4-methoxyphenyl)-2-((methylamino)methyl)cyclopropanecarboxylic acid,
(1R,2R)-methyl 1-(2-methoxyphenyl)-2-((methylamino)methyl)cyclopropanecarboxylate,
(1R,2R)-1-(2-methoxyphenyl)-2-((methylamino)methyl)cyclopropanecarboxylic acid,
(1R,2R)-methyl 2-((methylamino)methyl)-1-(naphthalen-2-yl)cyclopropanecarboxylate,
(1R,2R)-2-((methylamino)methyl)-1-(naphthalen-2-yl)cyclopropanecarboxylic acid,
(1R,2R)-methyl 1-([1,1'-biphenyl]-4-yl)-2-((methylamino)methyl)cyclopropanecarboxylate, and
(1R,2R)-1-([1,1'-biphenyl]-4-yl)-2-((methylamino)methyl)cyclopropanecarboxylic acid, or salts thereof.

In certain embodiments, the disclosure relates to compounds disclosed herein substituted with one or more substituents.

Compound Preparation

Methods for the preparation of certain cyclopropyl derivatives are disclosed in Pelphrey et al., Chem. Sci., 2010, 1, 254-257, Davies et al., Tetrahedron Letters, (1996) 37(24), 4133-4136, Denton & Davies, Organic Letters, (2009) 11(4), 787-790, Davies & Denton, Chem. Soc. Rev., 2009, 38, 3061-3071. See also U.S. Pat. No. 4,567,288, U.S. Pat. No. 7,385,064, and U.S. Published Application No. 2008/0051604 all hereby incorporated by reference.

In certain embodiments, the disclosure relates to a process of producing a compound of formula I comprising mixing a metal catalyst, a compound of formula II,

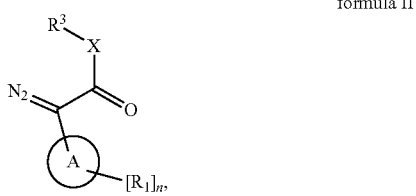

formula II and a compound of formula III,

formula III under conditions such that a compound of formula I is formed. In certain embodiments a compound of formula IA, IB, IC, or IC is formed. In certain embodiments, the metal catalyst is a chiral catalyst such as $Rh_2(S\text{-biTISP})_2$, $Rh_2(S\text{-DOSP})_4$, or $Rh_2(S\text{-PTAD})_4$.

Therapeutic Applications

In some embodiments, the disclosure relates to methods of treating or preventing mental disorders with pharmaceutical compositions disclosed herein administered to subject in need thereof. Examples of mental disorders include, but are not limited to, anxiety or mood disorders, depression, major depression disorder; schizophrenia, paranoid, undifferentiates, residual, catatonic or disorganized, subchronic or chronic with acute exacerbation, in remission; delusional (paranoid) disorder; brief reactive psychosis; schizophreniform disorder; schizoaffective disorder; induced psychotic disorder; atypical psychosis; personality disorders, paranoid, schizoid, schizotypal, antisocial; and bipolar disorders, maniac, hypomaniac, dysthymic or cyclothymic disorders; substance-induced major depression; and substance-induced psychotic disorder. Also included are adjustment disorders, eating disorders, sleep disorders, sexual identity disorders, and impulse control disorders.

In anxiety disorders, anxiety interferes with normal functioning. Representative classifications include specific phobias, generalized anxiety disorder, social anxiety disorder, panic disorder, agoraphobia, obsessive-compulsive disorder and post-traumatic stress disorder.

Subjects with mood disorders typically report intense and sustained sadness, melancholia or despair. Diagnosis can range from depression, major depression or clinical depression (milder but still prolonged depression can be diagnosed as dysthymia). Bipolar disorder (also known as manic depression) involves abnormally "high" or pressured mood states, known as mania or hypomania, alternating with normal or depressed mood.

Representative psychotic disorders include schizophrenia, and delusional disorder. Subjects with these disorders typically exhibit patterns of disbelief and often language use and perception can become disordered (e.g. delusions, thought disorder, hallucinations). Schizoaffective disorder is a category used for individuals showing aspects of both schizophrenia and affective disorders. Schizotypy is a category used for individuals showing some of the characteristics associated with schizophrenia but without meeting cut-off criteria.

Personality may be considered disordered if judged to be abnormally rigid and maladaptive. Representative personality disorders include those sometimes classed as eccentric (e.g. paranoid, schizoid and schizotypal personality disorders), to those sometimes classed as dramatic or emotional (antisocial, borderline, histrionic or narcissistic personality disorders) or those seen as fear-related (avoidant, dependent, or obsessive-compulsive personality disorders).

Eating disorders involve disproportionate concern in matters of food and weight. Categories of disorder in this area include anorexia nervosa, bulimia nervosa, exercise bulimia or binge eating disorder.

Sleep disorders such as insomnia involve disruption to normal sleep patterns, or a feeling of tiredness despite sleep appearing normal.

Sexual and gender identity disorders may be diagnosed, including dyspareunia, gender identity disorder and ego-dystonic homosexuality. Various kinds of paraphilia are considered mental disorders (sexual arousal to objects, situations, or individuals that are considered abnormal or harmful to the person or others).

Subjects with impulse control disorder are abnormally unable to resist certain urges or impulses. Representative examples include tic disorders such as Tourette's syndrome, and disorders such as kleptomania or pyromania, and gambling addiction.

Subjects with dissociative identity disorder suffer disturbances of their self-identity, memory and general awareness of themselves and their surroundings. Representative examples include depersonalization disorder or dissociative identity disorder itself (which has also been called multiple personality disorder, or "split personality), memory or cognitive disorders include amnesia or various kinds of old age dementia.

Representative childhood disorders autism spectrum disorders, oppositional defiant disorder and conduct disorder, and attention deficit hyperactivity disorder (ADHD).

In some embodiments, the disclosure relates to the management of neuropathic pain comprising administering a pharmaceutical composition disclosed herein to a subject at risk of, exhibiting symptoms or diagnosed with neuropathic pain. Neuropathic pain refers to pain associated with abnormal sensations sometimes called dysesthesias, which occur spontaneously and allodynias. Neuropathic pain may have continuous and/or episodic (paroxysmal) components. Common qualities of neuropathic pain include burning or coldness, "pins and needles" sensations, numbness and itching. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Central neuropathic pain is typically found in subjects with spinal cord injury, multiple sclerosis, and strokes. Common causes of painful peripheral neuropathies are herpes zoster infection, HIV-related neuropathies, nutritional deficiencies, toxin exposures, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of chemotherapy, radiation injury or surgery.

In some embodiments, the disclosure relates to the management of fibromyalgia comprising administering a pharmaceutical composition disclosed herein to a subject at risk of, exhibiting symptoms or diagnosed with fibromyalgia. Fibromyalgia is a medical disorder characterized by chronic widespread pain and a heightened and painful response to pressure.

In some embodiments, the disclosure relates to the management of pain from menstrual cramps comprising administering a pharmaceutical composition disclosed herein to a woman.

Pharmaceutical Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds contain a hydrogen-donating heteroatom (e.g. NH), this disclosure contemplates salts and/or isomers formed by transfer of said hydrogen atom to a basic group or atom within the molecule, such as in the case of an amino acid.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087, and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular, spinal, epidural, or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087, and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous, spinal, epidural, or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. A barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Combination Therapies

With regard to mental disorders, compounds disclosed herein may be administer in combinations with other psychiatric medications, such as antidepressants, anxiolytics, anticonvulsants, antipsychotics and stimulants such as anti-inflammatory agents.

Representative antidepressants include monoamine oxidase inhibitors (MAOIs), tricyclic antidepressants (TCAs), tetracyclic antidepressants (TeCAs), selective serotonin reuptake inhibitors (SSRIs), serotonin-norepinephrine reuptake inhibitors (SNRIs) and others.

Representative selective and non-selective MAOIs include benmoxin, hydralazine, iproclozide, iproniazid, isocarboxazid, isoniazid, mebanazine, nialamide, octamoxin, phenelzine, pheniprazine, phenoxypropazine, pivalylbenzhydrazine, procarbazine, safrazine, caroxazone, echinopsidine, furazolidone, linezolid, tranylcypromine, brofaromine, metralindole, minaprine, moclobemide, pirlindole, toloxatone, lazabemide, pargyline, rasagiline, selegiline, resveratrol, curcumin, catechin, desmethoxyyangonin, epicatechin, hydroxytyrosol, and piperine.

Representative TCAs include amitriptyline, amitriptylinoxide, butriptyline, clomipramine, demexiptiline, desipramine, dibenzepin, dimetacrine dosulepin/dothiepin, doxepin, imipramine, imipraminoxide, lofepramine, melitracen, metapramine, nitroxazepine, nortriptyline, noxiptiline, pipofezine, propizepine, protriptyline, quinupramine, amineptine, iprindole, opipramol, tianeptine, trimipramine. Representative TeCAs include, amoxapine, maprotiline, mazindol, mianserin, mirtazapine, setiptiline, ciclazindol, esmirtazapine, and oxaprotiline.

Representative SSRIs include citalopram, dapoxetine, escitalopram, fluoxetine, fluvoxamine, indalpine, paroxetine, sertraline, and zimelidine.

Representative SNRIs include venlafaxine, desvenlafaxine, duloxetine, milnacipran, levomilnacipran, sibutramine, and bicifadine.

Other representative anti-depressants include mianserin, mirtazapine, atomoxetine, mazindol, reboxetine, viloxazine, bupropion, tianeptine, and agomelatine.

Representative anxiolytics include alprazolam, chlordiazepoxide, clonazepam, diazepam, lorazepam, buspirone, tandospirone, gepirone, hydroxyzine, and pregabalin.

Representative anticonvulsants include lithium, valproic acid, lamotrigine, carbamazepine, oxcarbazepine, and gabapentin.

Representative antipsychotics include haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, and cannabidiol.

Representative stimulants include caffeine nicotine, amphetamine, methamphetamine, methylenedioxymethamphetamine, troparil, lometopane, methylphenidate, bupropion atomoxetine, reboxetine, modafinil, ampalex, carphedon, and yohimbine.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

In other embodiments, the compounds are administered in combination with medications that prevent indigestion or gastritis such as H2 receptor antagonists (cimetidine, ranitidine, famotidine, and nizatidine) or proton pump inhibitors such as omeprazole, lansoprazole, dexlansoprazole, esomeprazole, pantoprazole, and rabeprazole.

These compounds could be co-administered with analgesics to treat acute or chronic pain conditions. Examples of such analgesics would be opioid agonists (including morphine, codeine, methadone, meperidine, etc.), $\alpha_2$-adrenergic agonists (such as clonidine), gabapentin, and cholinesterase inhibitors (such as donepezil).

Terms

When describing the compounds for use in the disclosure, the terms used are to be construed in accordance with the following definitions, unless a context dictates otherwise.

A "chiral metal catalyst" refers to a catalytic metal complex where the ligands have one or more chiral centers. Examples include chiral 2-(2-aryl- or 2-alkyl-sufonylamino) phenyl-4-phenyl-1,3-oxazolines as ligands for copper-catalyzed enantioselective cyclopropanation reaction of olefins described in Ichiyanagi et al, Tetrahedron, 1997, 53(28), 9599-9610 and $Rh_2(S-biTISP)_2$, $Rh_2(S-DOSP)_4$, or $Rh_2(S-PTAD)_4$ catalysts as disclosed in Denton & Davis, Organic Letters, 2009, 11(4), 787-790, Davis et al., Tetrahedron Letters, 1996, 37(24) 4133-4136, and U.S. Pat. No. 7,385,064 hereby incorporated by reference. Chiral copper, rhodium, and ruthenium catalysts are representative of those contemplated by this disclosure. Typically, the chiral centers in the ligands induce catalytic conversion in enantiomeric or diastereomeric excess if present in the reaction product. Replacing the chiral ligands with their enantiomers will typically invert the stereochemistry of the reaction product.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above with the indicated number of carbon atoms attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

A "mental disorder" or "mental illness" or "mental disease" or "psychiatric or neuropsychiatric disease or illness or disorder" refers to mood disorders (e.g., depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV).

EXPERIMENTAL

General Information $^1$H Nuclear Magnetic Resonance (NMR) spectra were typically recorded on a Varian spectrometer at either 300, 400, 500, or 600 MHz, and $^{13}$C NMR at either 75, 100, or 125 MHz with the sample solvent being CDCl$_3$. The following abbreviations are used to explain multiplicities: s, singlet; d, doublet; t, triplet; q, quartet; dd, doublet of doublet; m, multiplet. Coupling constants were taken directly from the spectra and are uncorrected. IR spectra were obtained using a Thermo Scientific Nicolet iS10 FT-IR and reported in units of cm$^{-1}$. Melting points were measured on an electrothermal melting point apparatus and are uncorrected. High Resolution Mass spectral (HRMS) determinations (pos-APCI) were performed by the Instrument Center of the Department of Chemistry, Emory University. Elemental analysis was performed at Atlantic Microlabs Inc., Norcross Ga. Optical rotations were measured at the sodium D line (589 nm) and reported as follows: $[\alpha]D^{25}$, concentration (c in g/100 mL) and solvent. All rotations are measured at 25.0° C. Enantiomeric excess was determined by Varian Pro Star high performance liquid chromatography (HPLC) using chiral analytical columns (Chiralcel OD, Chiralcel OD-H, Chiralcel OJ, Chiralpak AD-H, Chiralpak AS-H, Chiralpack AD-RH, (R,R)-Whelk, or (S,S)-Whelk)(UV detection at 254 or 273 nm). Chiral columns and conditions are specified for individual compounds. Analytical TLC was performed on 0.25 mm E. Merck silica gel (60F-254) plates using UV light. Phosphomolybdic acid (PMA), KMnO$_4$, Ninhydrin or dinitrophenylhydrazine (DNP) was used as visualizing agent if necessary.

Glassware was dried in an oven overnight prior to use. Reactions were typically conducted under an atmosphere of argon. Flash column chromatography was performed on Merck silica gel 60 (230-400 mesh). Hexanes, toluene, THF, DCM, Diethyl ether and acetonitrile were dried by passage through activated alumina columns in a solvent purification system prior to use. All other reagents were purchased from Aldrich, Alfa Aesar, or Acros chemical companies and used without additional purification unless noted. Rhodium catalysts like Rh$_2$(OAc)$_4$, Rh$_2$(S-DOSP)$_4$, Rh$_2$(R-DOSP)$_4$, Rh$_2$(S-PTAD)$_4$, were obtained from lab sources and were used as is.

(E)-buta-1, 3-dienylbenzene (1)

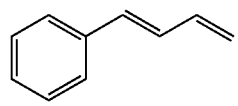

Methyltriphenylphosphine bromide (178 g, 50 mmol) was added to a flame dried 1 L flask and THF (500 mL) was added. The reaction flask was cooled to 0° C. and Potassium ter-butoxide (84 g, 75 mmol) and stirred for 5 hours at 0° C. (E)-3-phenylacrylaldehyde (66 g, 50 mmol) in THF (100 mL) was added drop wise over 1 h, then stirred for 16 additional hours. The reaction was poured into H$_2$O (1 L) and extracted into pentane (3×200 mL). The combined organic layers were washed with brine, dried over MgSO$_4$. Hexane was added to the reaction flask. Triphenyl phosphine oxide precipitates out. The reaction mixture was filtered through celite/silica gel and the solvent was removed under reduced pressure. The crude material was purified using Kughlerrohr distillation (85° C.) to obtain product as a colorless oil in 87% yield (56 g). $^1$H NMR (500 MHz, CDCl$_3$): δ7.32 (m, 5H), 6.78 (dd, J=10.4 Hz, 1H), 6.54 (m, 2H), 5.34 (d, J=16.8 Hz, 1H), 5.17 (d, J=10.4 Hz, 1H).

Synthesis of aryl diazoacetates (2)

Methyl 2-diazo-2-phenyl acetate (2a)

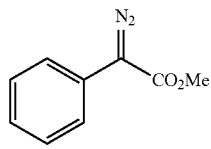

This was prepared according to a modified procedure provided in Baum et al., Synth. Commun. 1987, 17, 1709-16 hereby incorporated by reference. Methyl phenylacetate (4.5 g, 30 mmol) and p-acetamidobenzene sulfonyl azide (p-ABSA) (7.93 g, 33 mmol) were dissolved in acetonitrile (100 mL) and cooled to 0° C. in an ice bath. 1,8-Diazabicycloundec-7-ene (DBU) (5.48 mL, 36 mmol) was added in one portion and the reaction was stirred at 0° C. for 1 hour, then 3 additional hours at room temperature. The reaction was poured into saturated $NH_4Cl$ solution (100 mL) and extracted into diethyl ether (2×100 mL). The combined ether layers were dried over $MgSO_4$, filtered and concentrated to obtain the crude product. The crude material was purified by column chromatography ($SiO_2$, 95:5 petroleum ether/diethyl ether) to obtain 4.59 g (80% yield) of colored oil. $^1$H NMR (500 MHz, $CDCl_3$): δ3.84 (s, 3H), 7.46 (m, 5H).

Methyl 2-(4-bromophenyl)-2-diazoacetate (2b)

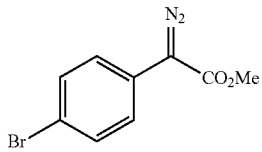

In a flame dried round bottom flask, 2-(4-bromophenyl) acetic acid (50 mmol, 1 eq.) was dissolved in MeOH (50 mL) and cooled to 0° C. Acetyl chloride (60 mmol, 1.2 eq.) was added drop wise at 0° C. The resultant reaction mixture was stirred at rt for overnight. The reaction mixture was poured in to a separation funnel having ethyl ether and saturated $NH_4Cl$ solution. Extracted twice; combined organic layers were washed with brine, dried over $MgSO_4$ and concentrated in vacuo. The crude methyl acetate mixture was taken to next step without further purification.

The resultant methyl acetate was dissolved in acetonitrile and p-acetamidobenzene sulfonyl azide (p-ABSA)(60 mmol, 1.2 eq.) was added. The reaction mixture was cooled to 0° C. and 1,8-Diazabicycloundec-7-ene (DBU) (120 mmol, 2 eq.) was added drop wise at 0° C. The reaction mixture was stirred at rt for overnight. Reaction mixture was quenched with saturated aqueous $NH_4Cl$ solution, extracted twice with diethyl ether (2×100 mL); combined organic layers were washed with brine, dried over anhydrous $MgSO_4$ and concentrated in vacuo. The residue was purified by flash chromatography on silica gel using 9:1 hexane/$Et_2O$ as eluant to isolate 11.16 g (93% yield) of yellow crystalline solid. $^1$H NMR (400 MHz, $CDCl_3$) □ 3.87 (s, 3H) 7.36 (d, J=8.61 Hz, 2H) 7.50 (d, J=8.61 Hz, 2H).

Methyl 2-([1,1'-biphenyl]-4-yl)-2-diazoacetate (2c)

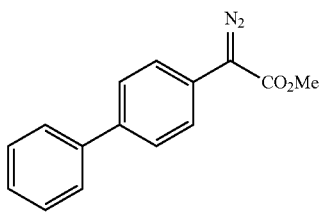

In a flame dried round bottom flask, 2-([1,1'-biphenyl]-4-yl) acetic acid (50 mmol, 1 eq.) was dissolved in MeOH (50 mL) and cooled to 0° C. Acetyl chloride (60 mmol, 1.2 eq.) was added drop wise at 0° C. The resultant reaction mixture was stirred at rt for overnight. The reaction mixture was poured in to a separation funnel having ethyl ether and saturated $NH_4Cl$ solution. Extracted twice; combined organic layers were washed with brine, dried over $MgSO_4$ and concentrated in vacuo. The crude methyl acetate mixture was taken to next step without further purification.

The resultant methyl acetate was dissolved in acetonitrile and p-acetamidobenzene sulfonyl azide (p-ABSA)(60 mmol, 1.2 eq.) was added. The reaction mixture was cooled to 0° C. and 1,8-Diazabicycloundec-7-ene (DBU) (120 mmol, 2 eq.) was added drop wise at 0° C. The reaction mixture was stirred at rt for overnight. Reaction mixture was quenched with saturated aqueous $NH_4Cl$ solution, extracted twice with diethyl ether (2×100 mL); combined organic layers were washed with brine, dried over anhydrous $MgSO_4$ and concentrated in vacuo. The residue was purified by flash chromatography on silica gel using 9:1 hexane/$Et_2O$ as eluant to isolate 9.6 g (80% yield) of yellow crystalline solid. $^1$H NMR (400 MHz, $CDCl_3$) □ 3.90 (s, 3H) 7.33-7.39 (m, 1H) 7.45 (t, J=7.63 Hz, 2H) 7.54-7.66 (m, 6H).

Methyl 2-diazo-2-(naphthalene-2-yl) acetate (2d)

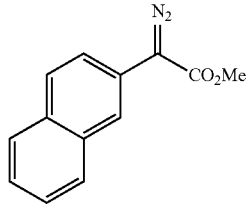

2-(Naphthalen-2-yl)acetic acid (5.00 g, 24.8 mmol) was dissolved in methanol (90 mL). Acetyl chloride (3.68 g, 46.8 mmol) was then added and the reaction was stirred overnight. The reaction was concentrated to obtain the crude acetate in 97% yield (5.25 g). This compounds was used without further purification. $^1$H NMR (500 MHz, $CDCl_3$) δ 3.70 (s, 3H), 3.75 (m, 2H), 7.40 (d, J=8.5 Hz, 1H), 7.44 (m, 2H), 7.72 (s, 1H), 7.80 (m, 3H).

Methyl 2-(naphthalen-2-yl)acetate (5.00 g, 24.9 mmol) and p-ABSA (7.49 g, 31.2 mmol) were dissolved in acetonitrile (35 mL) and cooled to 0° C. DBU (7.51 mL, 49.9 mmol) was added in one portion and the reaction was stirred at 0° C. for 1 hour, then 3 additional hours at room temperature. The reaction was poured into saturated $NH_4Cl$ solution and extracted into diethyl ether. The combined ether layers were dried over $MgSO_4$, filtered and concentrated to obtain the crude product. The crude material was purified by column chromatography ($SiO_2$, 95:5 petroleum ether/diethyl ether) to obtain 4.59 g (80% yield) of yellow crystalline solid. $^1$H NMR (400 MHz, $CDCl_3$) δ 3.92 (s, 3H) 7.42-7.51 (m, 2H) 7.54 (dd, J=8.80, 1.76 Hz, 1H) 7.81 (d, J=8.22 Hz, 2H) 7.86 (d, J=8.61 Hz, 1H) 8.02 (s, 1H).

Methyl 2-diazo-2-(3,4-dichlorophenyl) acetate (2e)

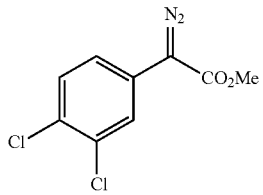

3,4-Dichlorophenylacetic acid (5.50 g, 26.8 mmol) was dissolved in MeOH (100 mL). Acetyl chloride (4.21 g, 53.7 mmol) was then added and the reaction was stirred overnight. The reaction was concentrated to obtain the crude acetate in 93% yield (5.47 g). This compound was used without further purification. $^1$H NMR (500 MHz, CDCl$_3$) δ 3.61 (m, 2H), 3.79 (s, 3H), 7.14 (d, 2H, J=8.5 Hz), 7.42 (d, 2H, J=8.5 Hz).

Methyl 2-(3,4-dichlorophenyl) acetate (5.33 g, 24.3 mmol) and p-ABSA (7.03 g, 30.4 mmol) were dissolved in acetonitrile (35 mL) and cooled to 0° C. DBU (7.40 mL, 48.7 mmol) was added in one portion and the reaction was stirred at 0° C. for 1 hour, then 3 additional hours at room temperature. The reaction was poured into saturated NH$_4$Cl solution and extracted into diethyl ether. The combined ether layers were dried over MgSO$_4$, filtered and concentrated to obtain the crude product. The crude material was purified by column chromatography (SiO$_2$, 95:5 petroleum ether/diethyl ether) to obtain 4.96 g (83% yield) of yellow crystalline solid. $^1$H NMR (400 MHz, CDCl$_3$) δ 3.88 (s, 3H) 7.29 (dd, J=8.61, 2.35 Hz, 1H) 7.43 (d, J=8.61 Hz, 1H) 7.64 (d, J=1.96 Hz, 1H).

Methyl 2-(2-chlorophenyl)-2-diazoacetate (2f)

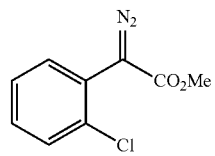

In a flame dried round bottom flask, 2-(2-chlorophenyl) acetic acid (55 mmol, 1 eq.) was dissolved in MeOH (100 mL) and cooled to 0° C. Acetyl chloride (66 mmol, 1.2 eq.) was added drop wise at 0° C. The resultant reaction mixture was stirred at rt for overnight. The reaction mixture was poured in to a separation funnel having ethyl ether and saturated NH$_4$Cl solution. Extracted twice; combined organic layers were washed with brine, dried over MgSO$_4$ and concentrated in vacuo. The crude methyl acetate mixture was taken to next step without further purification.

The resultant methyl acetate was dissolved in acetonitrile and p-acetamidobenzene sulfonyl azide (p-ABSA)(66 mmol, 1.2 eq.) was added. The reaction mixture was cooled to 0° C. and 1,8-Diazabicycloundec-7-ene (DBU) (110 mmol, 2 eq.) was added drop wise at 0° C. The reaction mixture was stirred at rt for overnight. Reaction mixture was quenched with saturated aqueous NH$_4$Cl solution, extracted twice with diethyl ether (2×100 mL); combined organic layers were washed with brine, dried over anhydrous MgSO$_4$ and concentrated in vacuo. The residue was purified by flash chromatography on silica gel using 9:1 hexane/Et$_2$O as eluant to isolate 10.16 g (87% yield) of yellow crystalline solid. $^1$H NMR (400 MHz, CDCl$_3$) □ 3.85 (s, 3H) 7.23-7.36 (m, 2H) 7.43 (d, J=7.43 Hz, 1H) 7.54 (d, J=7.04 Hz, 1H).

Methyl 2-diazo-2-(3,4-dimethoxyphenyl)acetate (2g)

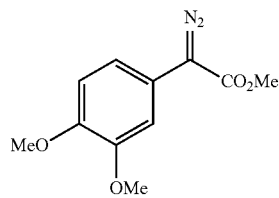

In a flame dried round bottom flask, 2-(3,4-dimethoxyphenyl) acetic acid (50 mmol, 1 eq.) was dissolved in MeOH (100 mL) and cooled to 0° C. Acetyl chloride (60 mmol, 1.2 eq.) was added drop wise at 0° C. The resultant reaction mixture was stirred at rt for overnight. The reaction mixture was poured in to a separation funnel having ethyl ether and saturated NH$_4$Cl solution. Extracted twice; combined organic layers were washed with brine, dried over MgSO$_4$ and concentrated in vacuo. The crude methyl acetate mixture was taken to next step without further purification.

The resultant methyl acetate was dissolved in acetonitrile and p-acetamidobenzene sulfonyl azide (p-ABSA)(60 mmol, 1.2 eq.) was added. The reaction mixture was cooled to 0° C. and 1,8-Diazabicycloundec-7-ene (DBU) (120 mmol, 2 eq.) was added drop wise at 0° C. The reaction mixture was stirred at rt for overnight. Reaction mixture was quenched with saturated aqueous NH$_4$Cl solution, extracted twice with diethyl ether (2×100 mL); combined organic layers were washed with brine, dried over anhydrous MgSO$_4$ and concentrated in vacuo. The residue was purified by flash chromatography on silica gel using 9:1 hexane/Et$_2$O as eluant to isolate 11.12 g (94% yield) of yellow crystalline solid. $^1$H NMR (400 MHz, CDCl$_3$) δ 3.86 (s, 3H) 3.88 (s, 3H) 3.90 (s, 3H) 6.87-6.90 (m, 1H) 7.19 (d, J=1.17 Hz, 1H) 7.26 (s, 1H).

Synthesis of styrylcyclopropanecarboxylates (3)

(E)-methyl 1-phenyl-2-styrylcyclopropanecarboxylate (3a)

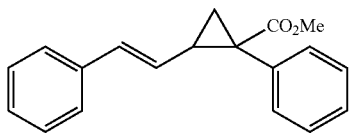 [SMILES: COC(=O)C1(c2ccccc2)CC1/C=C/c1ccccc1]

A solution of methyl 2-diazo-2-phenylacetate (176 mg, 1 mmol, and 1 eq.) in toluene (10 mL) was added by syringe pump over 1 h to a solution of (E)-buta-1, 3-dienylbenzene (390.2 mg, 3 mmol, 3 eq.) and Rh$_2$(OAc)$_4$ (0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 163 mg (93% yield) of oily liquid. $^1$H NMR (500

MHz, CDCl$_3$): δ 1.42 (m, 1H), 2.02 (m, 1H), 2.66 (m, 1H), 3.52 (s, 3H), 5.18 (dd, J=15.5 Hz, 10.0 Hz, 1H), 6.52 (d, J=15.5 Hz, 1H), 7.05 (m, 3H), 7.12 (m, 2H), 7.25 (m, 5H), $^{13}$C NMR (300 MHz, CDCl$_3$): δ 22.26 (CH$_2$), 31.65 (CH), 35.47 (C), 52.12 (CH$_3$), 125.6 (CH), 126.8 (CH), 127.0 (CH), 127.8 (CH), 128.1 (CH), 128.5 (CH), 131.0 (CH), 131.4 (CH), 135.6 (C), 136.8 (C), 173.7 (C), FTIR (neat): 1717, 1271, 1244, 1193, 1159, 960, 752, 694 cm$^{-1}$. HRMS (EI) m/z calcd for [C$_{19}$H$_{18}$O$_2$Na$_1$]$^+$ 301.1199. Found: 301.1194.

(E)-methyl 1-(4-bromophenyl)-2-styrylcyclopropanecarboxylate (3b)

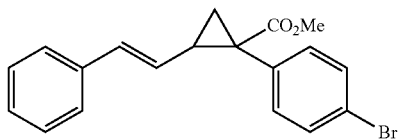 [SMILES: COC(=O)C1(c2ccc(Br)cc2)CC1/C=C/c1ccccc1]

A solution of methyl 2-(4-bromophenyl)-2-diazoacetate (510 mg, 2 mmol, and 1 eq.) in toluene (10 mL) was added by syringe pump over 1 h to a solution of (E)-buta-1,3-dienylbenzene (781 mg, 6 mmol, 3 eq.) and Rh$_2$(OAc)$_4$ (8 mg, 0.02 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 671 mg (94% yield) of oily liquid. $^1$H NMR (400 MHz, CDCl$_3$) δ 1.40 (dd, J=6.41, 4.88 Hz, 1H) 2.04 (dd, J=8.85, 4.58 Hz, 1H) 2.62-2.73 (m, 1H) 3.59 (s, 3H) 5.17 (dd, J=15.87, 9.76 Hz, 1H) 6.55 (d, J=15.87 Hz, 1H) 7.03-7.27 (m, 7H) 7.41 (d, J=8.24 Hz, 2H); $^{13}$C NMR (75 MHz, CDCl$_3$): δ 22.42, 31.83, 34.95, 52.42, 121.36, 125.75, 127.13, 127.98, 128.36, 131.11, 131.67, 133.20, 134.81, 136.72, 173.35; FTIR (Neat): 1716, 1488, 1270, 1242, 728 cm$^{-1}$; HRMS (pos-APCI) calcd for C$_{19}$H$_{18}$O$_2^{79}$Br: 357.04847. Found 357.04834; HRMS (neg-APCI) calcd for C$_{19}$H$_{16}$O$_2^{79}$Br: 355.03391. Found 355.03397.

(E)-methyl 1-([1,1'-biphenyl]-4-yl)-2-styrylcyclopropanecarboxylate (3c)

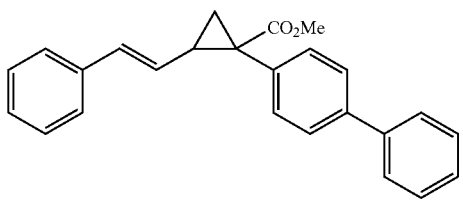 [SMILES: COC(=O)C1(c2ccc(-c3ccccc3)cc2)CC1/C=C/c1ccccc1]

A solution of methyl 2-([1,1'-biphenyl]-4-yl)-2-diazoacetate (252 mg, 1 mmol, and 1 eq.) in toluene (10 mL) was added by syringe pump over 1 h to a solution of (E)-buta-1,3-dienylbenzene (390.2 mg, 3 mmol, 3 eq.) and Rh$_2$(OAc)$_4$ (4 mg, 0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 297 mg (84% yield) of oily liquid. $^1$H NMR (400 MHz, CDCl$_3$) δ 1.51 (dd, J=6.25, 4.73 Hz, 1H) 2.09 (dd, J=8.85, 4.58 Hz, 1H) 2.66-2.76 (m, 1H) 3.67 (s, 3H) 5.26 (dd, J=15.87, 9.76 Hz, 1H) 6.60 (d, J=15.87 Hz, 1H) 7.14 (t, J=7.78 Hz, 3H) 7.20 (d, J=7.02 Hz, 2H) 7.36 (d, J=7.93 Hz, 3H) 7.44 (t, J=7.63 Hz, 2H) 7.56 (d, J=8.24 Hz, 2H) 7.62 (d, J=7.02 Hz, 2H); $^{13}$C NMR (75 MHz, CDCl$_3$): δ 22.6, 32.1, 35.4, 52.6, 125.9, 126.7, 127.0, 127.1, 127.2, 128.4, 128.7, 128.8, 131.3, 132.0, 134.9, 137.1, 140.0, 140.7, 174.1; FTIR (Neat): 1716, 1487, 1270, 1243, 753 cm$^{-1}$; HRMS (pos-APCI) calcd for C$_{25}$H$_{23}$O$_2$: 355.16926. Found 355.16904.

(E)-methyl 1-(naphthalen-2-yl)-2-styrylcyclopropanecarboxylate (3d)

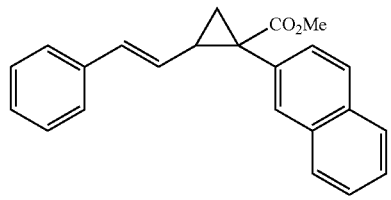 [SMILES: COC(=O)C1(c2ccc3ccccc3c2)CC1/C=C/c1ccccc1]

A solution of methyl 2-diazo-2-(naphthalen-2-yl)acetate (226 mg, 1 mmol, and 1 eq.) in toluene (10 mL) was added by syringe pump over 1 h to a solution of (E)-buta-1,3-dienylbenzene (390.2 mg, 3 mmol, 3 eq.) and Rh$_2$(OAc)$_4$ (4 mg, 0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 295 mg (90% yield) of oily liquid. NMR (400 MHz, CDCl$_3$) δ 1.59 (dd, J=6.41, 4.58 Hz, 1H) 2.12 (dd, J=9.00, 4.42 Hz, 1 H) 2.75 (td, J=9.31, 6.71 Hz, 1H) 3.58 (s, 3H) 5.20 (dd, J=15.87, 9.76 Hz, 1H) 6.60 (d, J=15.56 Hz, 1H) 7.01-7.14 (m, 5H) 7.42 (dt, J=6.41, 3.20 Hz, 3H) 7.72-7.81 (m, 4H); $^{13}$C NMR (75 MHz, CDCl$_3$) δ 22.6, 32.1, 35.7, 52.4, 125.7, 125.9, 126.9, 127.4, 127.5, 127.7, 128.3, 128.5, 129.9, 129.9, 131.3, 132.5, 133.0, 133.5, 136.9, 174.0; FT-IR (neat): 1715, 1434, 1270, 1244, 906, 728 cm$^{-1}$; HRMS (pos-APCI) calcd for C$_{23}$H$_{21}$O$_2$: 329.15361.
Found: 329.15347.

(E)-methyl 1-(3,4-dichlorophenyl)-2-styrylcyclopropanecarboxylate (3e)

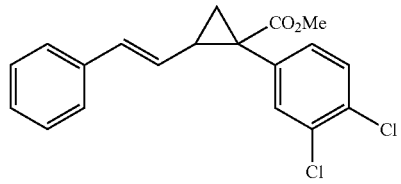 [SMILES: COC(=O)C1(c2ccc(Cl)c(Cl)c2)CC1/C=C/c1ccccc1]

A solution of methyl 2-diazo-2-(3,4-dichlorophenyl)acetate (490 mg, 2 mmol, and 1 eq.) in toluene (10 mL) was added by syringe pump over 1 h to a solution of (E)-buta-1,3-dienylbenzene (781 mg, 6 mmol, 3 eq.) and Rh$_2$(OAc)$_4$ (8 mg, 0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 659 mg (95% yield) of oily liquid. $^1$H NMR (400 MHz, CDCl$_3$) δ 1.42 (dd, J=6.56, 4.73 Hz, 1H) 2.06 (dd, J=9.00, 4.73 Hz, 1H) 2.68 (td, J=9.23, 6.86 Hz, 1H) 3.64 (s, 3H) 5.18 (dd, J=15.71, 9.61 Hz, 1H) 6.59 (d, J=15.87 Hz, 1H) 7.10-7.15 (m, 3H) 7.17 (d, J=7.02 Hz, 1H) 7.20-7.26 (m, 2H) 7.36 (d, J=8.24 Hz, 1H) 7.40 (d, J=1.83 Hz, 1H); $^{13}$C NMR (75 MHz, CDCl$_3$) δ 22.5, 32.0, 34.7, 52.6, 125.9, 127.3, 127.5, 128.4, 129.9, 131.2, 131.5, 132.0, 132.2, 133.3, 136.1, 136.7, 173.0; FT-IR (neat): 1717, 1473, 1272, 1241, 956, 753, 727 cm$^{-1}$; HRMS (pos-APCI) calcd for C$_{19}$H$_{15}$O$_2$$^{35}$Cl$_2$: 345.04546 Found: 345.04542.

(E)-methyl 1-(2-chlorophenyl)-2-styrylcyclopropanecarboxylate (3f)

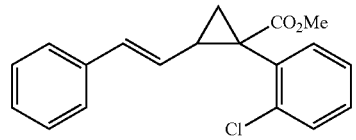 [SMILES: COC(=O)C1(c2ccccc2Cl)CC1/C=C/c1ccccc1]

A solution of methyl 2-(2-chlorophenyl)-2-diazoacetate (421 mg, 2 mmol, and 1 eq.) in toluene (10 mL) was added by syringe pump over 1 h to a solution of (E)-buta-1,3-dienylbenzene (781 mg, 6 mmol, 3 eq.) and Rh$_2$(OAc)$_4$ (8 mg, 0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 605 mg (97% yield) of oily liquid. $^1$H NMR (400 MHz, CDCl$_3$) δ 1.49 (br. s., 1H) 1.92 (br. s., 1H) 2.89 (br. s., 1H) 3.57 (s, 3H) 5.30 (br. s., 1H) 6.52 (d, J=15.56 Hz, 1H) 7.03-7.20 (m, 7H) 7.27-7.33 (m, 2H); $^{13}$C NMR (75 MHz, CDCl$_3$) δ 22.2, 32.2, 35.1, 52.34, 125.71, 126.28, 126.94, 128.24, 128.65, 129.38, 136.95, 137.00, 172.95; FT-IR (neat): 1718, 1434, 1268, 1241, 953, 748 cm$^{-1}$; HRMS (pos-APCI) calcd for C$_{19}$H$_{18}$O$_2$$^{35}$Cl$_1$: 313.09898 Found: 313.09897.

(E)-methyl 1-(3,4-dimethoxyphenyl)-2-styrylcyclopropanecarboxylate (3g)

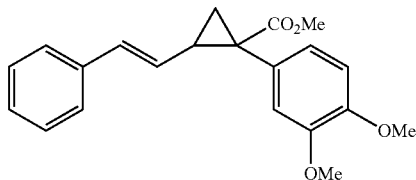 [SMILES: COC(=O)C1(c2ccc(OC)c(OC)c2)CC1/C=C/c1ccccc1]

A solution of methyl 2-diazo-2-(3,4-dimethoxyphenyl)acetate (472 mg, 2 mmol, and 1 eq.) in toluene (10 mL) was added by syringe pump over 1 h to a solution of (E)-buta-1,3-dienylbenzene (781 mg, 6 mmol, 3 eq.) and Rh$_2$(OAc)$_4$ (8 mg, 0.01 mmol, 0.1 eq.) in toluene (10 mL) at rt. The reaction mixture was stirred at rt for an additional 2 h, and then concentrated in vacuo. Crude reaction mixture was purified by flash chromatography on silica gel using 9:1 hexane/EtOAc as eluant to isolate 621 mg (92% yield) of oily liquid. $^1$H NMR (400 MHz, CDCl$_3$) δ 1.40-1.46 (m, 1H) 2.03 (dd, J=8.85, 4.27 Hz, 1H) 2.60-2.70 (m, 1H) 3.60 (s, 3H) 3.73 (s, 3H) 3.81 (s, 3H) 5.25 (dd, J=15.87, 9.76 Hz, 1H) 6.56 (d, J=15.87 Hz, 1H) 6.75-6.88 (m, 3H) 7.07-7.20 (m, 6H); $^{13}$C NMR (75 MHz, CDCl$_3$) δ 22.6, 31.6, 34.9, 52.0, 55.3, 55.3, 110.2, 114.5, 123.3, 125.4, 126.7, 127.9, 128.1, 128.7, 130.7, 136.7, 147.8, 147.9, 173.8 FT-IR (neat): 1715, 1516, 1246, 1226, 756, 727 cm$^{-1}$; HRMS (pos-APCI) calcd for C$_{21}$H$_{23}$O$_4$: 339.15909 Found: 339.15894.

Synthesis of formyl cyclopropanecarboxylates (4)

Methyl 2-formyl-1-phenylcyclopropanecarboxylate (4a)

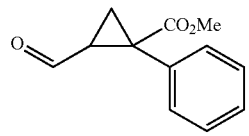 [SMILES: COC(=O)C1(c2ccccc2)CC1C=O]

Ozone was bubbled through a solution of (E)-methyl 1-phenyl-2-styrylcyclopropanecarboxylate (835 mg, 3 mmol, 1 eq.) in DCM (10 mL) at −78° C. until the blue color of ozone persists. The reaction mixture was warmed to rt and PPh$_3$ was added. The resultant mixture was stirred at rt for 2 h, and then concentrated in vacuo. Purified by flash chromatography on silica gel using 9:1 hexane/EtOAc as eluant to isolate 623 mg (86% yield) of oily liquid. $^1$H NMR (400 MHz, CDCl$_3$) δ 2.03-2.08 (m, 1H) 2.10 (dd, J=8.54, 4.88 Hz, 1H) 2.71 (dd, J=8.54, 6.41 Hz, 1H) 3.62 (s, 3H) 7.25-7.34 (m, 5H) 8.53 (d, J=6.41 Hz, 1H); $^{13}$C NMR (75 MHz, CDCl$_3$) δ 19.1, 36.1, 37.2, 52.8, 128.0, 128.4, 130.8, 133.5, 171.8, 198.1; FT-IR (neat): 1706, 1249, 1155, 699 cm$^{-1}$; HRMS (pos-APCI) calcd for C$_{15}$H$_{19}$O$_3$: 247.13287 Found: 247.13284.

Methyl 1-(4-bromophenyl)-2-formylcyclopropanecarboxylate (4b)

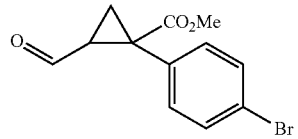

Ozone was bubbled through a solution of (E)-methyl 1-(4-bromophenyl)-2-styrylcyclopropanecarboxylate (535 mg, 1.5 mmol, 1 eq.) in DCM (10 mL) at −78° C. until the blue color of ozone persists. The reaction mixture was warmed to rt and PPh$_3$ was added. The resultant mixture was stirred at rt for 2 h, and then concentrated in vacuo. Purified by flash chromatography on silica gel using 9:1 hexane/EtOAc as eluant to isolate 401 mg (93% yield) of oily liquid. $^1$H NMR (400 MHz, CDCl$_3$) δ 2.01-2.08 (m, 1H) 2.12 (dd, J=8.70, 5.03 Hz, 1H) 2.77 (dt, J=8.54, 6.25 Hz, 1H) 3.65 (s, 3H) 7.18 (d, J=8.54 Hz, 2H) 7.42-7.52 (m, 2H) 8.64 (d, J=6.10 Hz, 1H); $^{13}$C NMR (75 MHz, CDCl$_3$): δ 19.0, 35.9, 36.7, 52.8, 121.9, 128.1, 129.8, 131.4, 132.4, 133.3, 171.1, 197.5; FTIR (Neat): 1707, 1450, 1250, 1157, 713 cm$^{-1}$; HRMS (pos-API) calcd for C$_{21}$H$_{10}$O$_4$Br: 296.97679. Found 296.97673.

Methyl 1-([1,1'-biphenyl]-4-yl)-2-formylcyclopropanecarboxylate (4c)

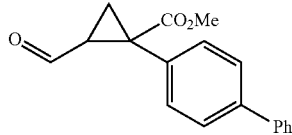 [SMILES: COC(=O)C1(c2ccc(-c3ccccc3)cc2)CC1C=O]

Ozone was bubbled through a solution of (E)-methyl 1-([1,1'-biphenyl]-4-yl)-2-styrylcyclopropanecarboxylate (531 mg, 1.5 mmol, 1 eq.) in DCM (10 mL) at −78° C. until the blue color of ozone persists. The reaction mixture was warmed to rt and $PPh_3$ was added. The resultant mixture was stirred at rt for 2 h, and then concentrated in vacuo. Purified by flash chromatography on silica gel using 9:1 hexane/EtOAc as eluant to isolate 355 mg (83% yield) of oily liquid. $^1$H NMR (400 MHz, $CDCl_3$) δ ppm 2.03-2.19 (m, 2H) 2.70-2.82 (m, 1H) 3.61 (s, 3H) 7.28-7.45 (m, 5H) 7.54 (dd, J=7.32, 6.10 Hz, 4H) 8.59 (d, J=6.41 Hz, 1H); $^{13}$C NMR (75 MHz, $CDCl_3$): δ 198.06, 171.7, 140.7, 140.0, 133.3, 132.4, 131.1, 129.8, 128.5, 128.2, 127.3, 127.0, 126.8, 52.7, 36.9, 36.1, 19.1; FTIR (Neat): 1707, 1487, 1249, 1155, 763 $cm^{-1}$; HRMS (Pos-API) calcd for $C_{18}H_{15}O_3$: 279.10267. Found 279.10253.

Methyl 2-formyl-1-(naphthalen-2-yl)cyclopropanecarboxylates (4d)

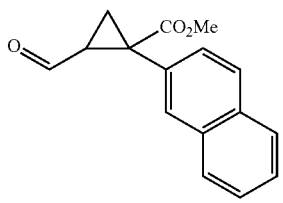 [SMILES: COC(=O)C1(c2ccc3ccccc3c2)CC1C=O]

Ozone was bubbled through a solution of (E)-methyl 1-(naphthalen-2-yl)-2-styrylcyclopropanecarboxylate (492 mg, 1.5 mmol, 1 eq.) in DCM (10 mL) at −78° C. until the blue color of ozone persists. The reaction mixture was warmed to rt and $PPh_3$ was added. The resultant mixture was stirred at rt for 2 h, and then concentrated in vacuo. Purified by flash chromatography on silica gel using 9:1 hexane/EtOAc as eluant to isolate 202 mg (53% yield) of oily liquid. $^1$H NMR (400 MHz, $CDCl_3$) δ 2.21 (d, J=7.63 Hz, 2H) 2.81 (q, J=7.22 Hz, 1H) 3.64 (s, 3H) 7.40 (dd, J=8.70, 1.07 Hz, 1H) 7.45-7.55 (m, 2H) 7.81 (d, J=8.24 Hz, 4H) 8.56 (d, J=6.71 Hz, 1H)$^{13}$C NMR (75 MHz, $CDCl_3$) δ 19.2, 36.0, 36.6, 53.0, 130.2, 130.3, 132.3, 132.4, 132.7, 133.8, 134.9, 139.3, 141.0, 141.2, 170.94, 197.05; FT-IR (neat): 1706, 1435, 1252, 1153, 733 $cm^{-1}$; HRMS (pos-APCI) calcd for $C_{16}H_{13}O_3$: 253.08702 Found: 253.08691.

Methyl 1-(3,4-dichlorophenyl)-2-formylcyclopropanecarboxylate (4e)

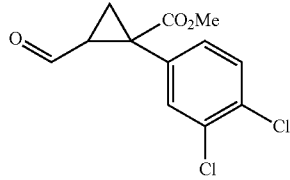 [SMILES: COC(=O)C1(c2ccc(Cl)c(Cl)c2)CC1C=O]

Ozone was bubbled through a solution of (E)-methyl 1-(3,4-dichlorophenyl)-2-styrylcyclopropanecarboxylate (520 mg, 1.5 mmol, 1 eq.) in DCM (10 mL) at −78° C. until the blue color of ozone persists. The reaction mixture was warmed to rt and $PPh_3$ was added. The resultant mixture was stirred at rt for 2 h, and then concentrated in vacuo. Purified by flash chromatography on silica gel using 9:1 hexane/EtOAc as eluant to isolate 331 mg (80% yield) of oily liquid. $^1$H NMR (400 MHz, $CDCl_3$) δ 2.03-2.08 (m, 1H) 2.13 (dd, J=8.70, 5.03 Hz, 1H) 2.80 (dt, J=8.47, 6.14 Hz, 1H) 3.67 (s, 3H) 7.14 (dd, J=8.24, 1.83 Hz, 1H) 7.39-7.45 (m, 2H) 8.74 (d, J=5.80 Hz, 1H); $^{13}$C NMR (75 MHz, $CDCl_3$) δ 19.2, 36.0, 36.6, 53.0, 130.3, 130.3, 132.3, 132.4, 132.7, 133.8, 170.9, 197.0; FT-IR (neat): 1707, 1474, 1247, 1159, 726 $cm^{-1}$; HRMS (pos-APCI) calcd for $C_{12}H_9O_3C_{12}$: 270.99342 Found: 270.99337.

Methyl 1-(2-chlorophenyl)-2-formylcyclopropanecarboxylate (4f)

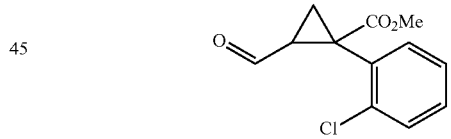

Ozone was bubbled through a solution of (E)-methyl 1-(2-chlorophenyl)-2-styrylcyclopropanecarboxylate (312 mg, 1 mmol, 1 eq.) in DCM (10 mL) at −78° C. until the blue color of ozone persists. The reaction mixture was warmed to rt and $PPh_3$ was added. The resultant mixture was stirred at rt for 2 h, and then concentrated in vacuo. Purified by flash chromatography on silica gel using 9:1 hexane/EtOAc as eluant to isolate 166 mg (70% yield) of oily liquid. $^1$H NMR (400 MHz, $CDCl_3$) δ 1.90-2.29 (m, 2H) 3.11 (br. s., 1H) 3.66 (s, 3H) 7.18-7.54 (m, 4H) 8.95 (br. s., 1H); $^{13}$C NMR (75 MHz, $CDCl_3$) δ 20.4, 36.1, 53.1, 127.0, 128.4, 129.5, 129.6, 130.1, 131.9, 133.6, 171.2, 196.2; FT-IR (neat): 1708, 1435, 1250, 1158, 727 $cm^{-1}$; HRMS (pos-APCI) calcd for $C_{12}H_{10}O_3Cl$: 237.03240 Found: 237.03194.

Synthesis of methylamino cyclopropanecarboxylates (5)

Methyl 2-((methylamino)methyl)-1-phenylcyclopropanecarboxylate (5a)

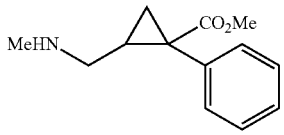 [SMILES: CNCC1CC1(C(=O)OC)c1ccccc1]

In a 100 mL round bottom flask equipped with a magnetic stir bar, methyl 2-formyl-1-phenylcyclopropanecarboxylate (612 mg, 3 mmol) was dissolved in methanol (50 mL) and flushed with argon. This solution was treated with methylamine (2M in MeOH, 3 mL, 6 mmol) and Ti(O-iPr)$_4$ (2.4 mL, 6 mmol) and stirred at room temperature for 16 hours. After the allotted time had passed, NaBH$_4$ (170 mg, 4.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give a colorless oil in 63% yield (416 mg). $^1$H NMR (400 MHz, CDCl$_3$) δ 1.24 (dd, J=6.41, 4.58 Hz, 1H) 1.74 (dd, J=9.15, 4.27 Hz, 1H) 1.90-2.00 (m, 1H) 2.02-2.14 (m, 1H) 2.32 (s, 3H) 2.45 (dd, J=12.36, 5.95 Hz, 1H) 3.62 (s, 3H) 7.15-7.49 (m, 5H); $^{13}$C NMR (75 MHz, CDCl$_3$) δ 20.0, 27.7, 33.0, 36.1, 52.1, 127.0, 127.8, 130.85, 135.61, 174.35; FT-IR (neat): 2949, 2843, 1715, 1434, 1251, 700 cm$^{-1}$; HRMS (pos-APCI) calcd for C$_{13}$H$_{18}$O$_2$N: 220.13321 Found: 220.13306.

Methyl 2-((methylamino)methyl)-1-phenylcyclopropanecarboxylate fumarate (5a salt)

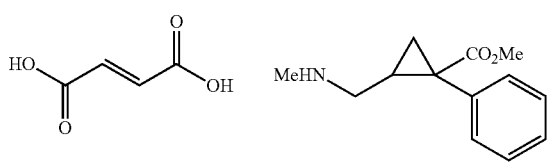 [SMILES: O=C(O)/C=C/C(=O)O ; CNCC1CC1(C(=O)OC)c1ccccc1]

Methyl 2-((methylamino)methyl)-1-phenylcyclopropanecarboxylate (471 mg, 2.1 mmol) was dissolved in isopropanol (20 mL) and then treated with fumaric acid (249 mg, 2.1 mmol) and stirred for 30 minutes at room temperature. The mixture was then concentrated under reduced pressure and the residue was re-dissolved in 2:1:1 isopropanol/hexanes/ethyl acetate (10 mL) and refluxed for 2 hours. The solution was cooled to room temperature and then to −20° C. using an acetone/ice bath. The resulting solid was filtered and washed with cold acetone to give off-white solid. $^1$H NMR (400 MHz, CD$_3$OD) δ 1.47-1.58 (m, 1H) 1.78 (dd, J=8.54, 4.88 Hz, 1H) 1.95 (dd, J=12.51, 10.98 Hz, 1H) 2.12-2.24 (m, 1H) 2.59 (s, 3H) 3.23 (dd, J=12.81, 3.97 Hz, 1H) 3.58 (s, 3H) 6.67 (s, 2H) 7.26-7.38 (m, 5H); $^{13}$C NMR (75 MHz, CD$_3$OD) δ 21.0, 23.5, 33.4, 33.4, 34.8, 51.1, 53.3, 129.1, 129.7, 132.3, 135.8, 136.3, 171.5, 175.0; FT-IR (neat): 3000, 1713, 1560, 1261, 1171, 702 cm$^{-1}$; HRMS (pos-APCI) calcd for C$_{13}$H$_{18}$O$_2$N: 220.13321 Found: 220.13298.

Methyl 1-(4-bromophenyl)-2-((methylamino)methyl)cyclopropanecarboxylate (5b)

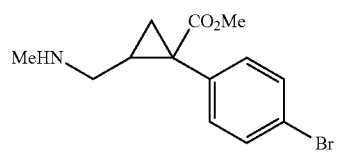 [SMILES: CNCC1CC1(C(=O)OC)c1ccc(Br)cc1]

In a 100 mL round bottom flask equipped with a magnetic stir bar, methyl 1-(4-bromophenyl)-2-formylcyclopropanecarboxylate (283 mg, 1 mmol) was dissolved in methanol (20 mL) and flushed with argon. This solution was treated with methylamine (2M in MeOH, 0.5 mL, 2 mmol) and Ti(O-iPr)$_4$ (0.4 mL, 2 mmol) and stirred at room temperature for 16 hours. After the allotted time had passed, NaBH$_4$ (56 mg, 1.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 56% yield (166 mg). $^1$H NMR (400 MHz, CDCl$_3$) δ 1.19 (dd, J=6.56, 4.42 Hz, 1H) 1.24 (br. s., 1H) 1.75 (dd, J=8.85, 4.27 Hz, 1H) 1.92-2.00 (m, 1H) 2.01-2.12 (m, 1H) 2.32 (s, 3H) 2.42 (dd, J=12.20, 5.80 Hz, 1H) 3.60 (s, 3H) 7.19 (d, J=8.24 Hz, 2H) 7.44 (d, J=8.24 Hz, 2H); $^{13}$C NMR (75 MHz, CDCl$_3$): δ 20.1, 27.7, 32.5, 36.2, 52.0, 52.2, 121.1, 131.0, 132.5, 134.7, 173.8; FTIR (Neat): 1707, 1474, 1247, 1159, 726 cm$^{-1}$; HRMS (Pos-APCI) calcd for C$_{12}$H$_9$O$_3$C$_{12}$: 270.99342. Found 270.99337.

Methyl 1-(4-bromophenyl)-2-((methylamino)methyl)cyclopropanecarboxylate fumarate (5b salt)

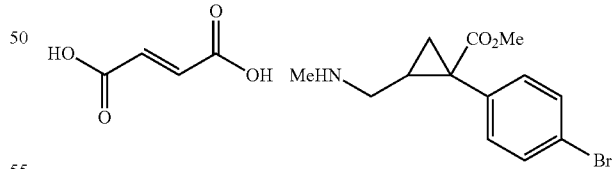

Methyl 1-(4-bromophenyl)-2-((methylamino)methyl)cyclopropanecarboxylate (298 mg, 1 mmol) was dissolved in isopropanol (20 mL) and then treated with fumaric acid (116 mg, 1 mmol) and stirred for 30 minutes at room temperature. The mixture was then concentrated under reduced pressure and the residue was re-dissolved in 2:1:1 isopropanol/hexanes/ethyl acetate (10 mL) and refluxed for 2 hours. The solution was cooled to room temperature and then to −20° C. using an acetone/ice bath. The resulting solid was filtered and washed with cold acetone to give off-white solid. $^1$H NMR (400 MHz, CD$_3$OD) δ 1.47-1.55 (m, 1H) 1.82 (dd, J=8.39, 4.73 Hz, 1H) 1.99 (dd, J=12.51, 10.98 Hz, 1H) 2.13-2.26 (m, 1H) 2.63 (s, 3H) 3.27 (dd, J=12.66, 3.81 Hz, 1H) 3.63 (s, 3H) 6.68 (s, 2H) 7.25 (d, J=8.24 Hz, 2H) 7.53 (d, J=8.24 Hz, 2H); $^{13}$C NMR (75 MHz, CD$_3$OD) δ 21.1, 23.6, 33.6, 34.3, 51.1, 53.4, 123.1, 132.8, 134.3, 135.1, 136.3, 171.5, 174.5; FT-IR (neat): 3027, 2954, 2768, 1720, 1262 cm$^{-1}$; HRMS (pos-APCI) calcd for $C_{13}H_{17}O_2N$: 298.04372 Found: 298.04364.

Methyl 1-([1,1'-biphenyl]-4-yl)-2-((methylamino)methyl)cyclopropanecarboxylate hydrochloride (5c salt)

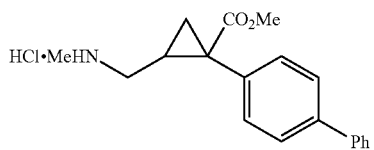

In a 100 mL round bottom flask equipped with a magnetic stir bar, methyl 1-([1,1'-biphenyl]-4-yl)-2-formylcyclopropanecarboxylate (280 mg, 1 mmol) was dissolved in methanol (20 mL) and flushed with argon. This solution was treated with methylamine (2M in MeOH, 0.5 mL, 2 mmol) and Ti(O-iPr)$_4$ (0.4 mL, 2 mmol) and stirred at room temperature for 16 hours. After the allotted time had passed, NaBH$_4$ (56 mg, 1.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 78% yield (230 mg). The product was dissolved in diethyl ether (15 mL), then treated with hydrochloric acid in diethyl ether (2M in diethyl ether, 1 mL), and the resulting white solid was filtered and washed with diethyl ether to obtain white solid. $^1$H NMR (400 MHz, CDCl$_3$) δ 1.27 (dd, J=6.41, 4.58 Hz, 1H) 1.65 (br. s., 1H) 1.76 (dd, J=8.70, 4.42 Hz, 1H) 1.95-2.04 (m, 1H) 2.05-2.13 (m, 1H) 2.31 (s, 3H) 2.48 (dd, J=12.20, 5.80 Hz, 1H) 3.60 (s, 3H) 7.29-7.37 (m, 3H) 7.38-7.45 (m, 2H) 7.56 (dd, J=16.78, 7.63 Hz, 4H); $^{13}$C NMR (75 MHz, CDCl$_3$) δ 20.1, 27.7, 32.7, 36.1, 52.0, 52.2, 126.6, 126.8, 127.0, 128.5, 131.2, 134.5, 139.8, 140.4, 174.3; FT-IR (neat): 1716, 1487, 1434, 1250, 1010, 763 cm$^{-1}$; HRMS (pos-APCI) calcd for $C_{19}H_{22}O_2N_1$: 296.16451.
Found: 296.16429.

Methyl 2-((methylamino)methyl)-1-(naphthalen-2-yl)cyclopropanecarboxylate hydrochloride (5d salt)

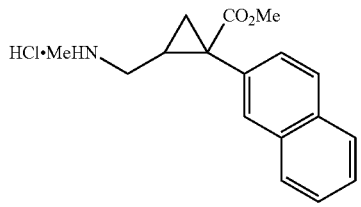

In a 100 mL round bottom flask equipped with a magnetic stir bar, methyl 2-formyl-1-(naphthalen-2-yl)cyclopropanecarboxylate (254 mg, 1 mmol) was dissolved in methanol (20 mL) and flushed with argon. This solution was treated with methylamine (2M in MeOH, 0.5 mL, 2 mmol) and Ti(O-iPr)$_4$ (0.4 mL, 2 mmol) and stirred at room temperature for 16 hours. After the allotted time had passed, NaBH$_4$ (56 mg, 1.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 60% yield (161 mg). The product was dissolved in diethyl ether (15 mL), then treated with hydrochloric acid in diethyl ether (2M in diethyl ether, 1 mL), and the resulting white solid was filtered and washed with diethyl ether to obtain white solid. $^1$H NMR (400 MHz, CDCl$_3$) δ 1.28 (br. s., 1H) 1.37 (dd, J=6.56, 4.42 Hz, 1H) 1.81 (dd, J=8.85, 4.27 Hz, 1H) 1.90-2.05 (m, 1H) 2.08-2.20 (m, 1H) 2.27 (s, 3H) 2.46 (dd, J=12.51, 6.10 Hz, 1H) 3.60 (s, 3H) 7.41-7.49 (m, 3H) 7.72 (s, 1H) 7.79 (d, J=8.54 Hz, 3H); $^{13}$C NMR (75 MHz, CDCl$_3$) δ 20.2, 28.0, 33.2, 36.2, 52.0, 52.2, 125.8, 125.9, 127.3, 127.4, 127.6, 129.1, 129.3, 132.4, 133.0, 133.3, 174.4; FT-IR (neat): 1715, 1433, 1255, 1165, 749 cm$^{-1}$; HRMS (pos-APCI) calcd for $C_{17}H_{20}O_2N$: 270.14886 Found: 270.14880.

Methyl 1-(3,4-dichlorophenyl)-2-((methylamino)methyl)cyclopropanecarboxylate (5e)

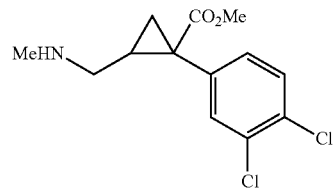 [SMILES: CNCC1CC1(C(=O)OC)c1ccc(Cl)c(Cl)c1]

In a 100 mL round bottom flask equipped with a magnetic stir bar, methyl 1-(3,4-dichlorophenyl)-2-formylcyclopropanecarboxylate (819 mg, 3 mmol) was dissolved in methanol (50 mL) and flushed with argon. This solution was treated with methylamine (2M in MeOH, 3 mL, 6 mmol) and Ti(O-iPr)$_4$ (2.4 mL, 6 mmol) and stirred at room temperature for 16 hours. After the allotted time had passed, NaBH$_4$ (170 mg, 4.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 57% yield (491 mg). $^1$H NMR (400 MHz, CDCl$_3$) δ 1.18 (dd, J=6.41, 4.58 Hz, 1H) 1.77 (dd, J=8.70, 4.42 Hz, 1H) 1.94-2.13 (m, 2H) 2.35 (s, 3H) 2.43 (dd, J=11.75, 5.34 Hz, 1H) 3.63 (s, 3H) 7.16 (dd, J=8.24, 1.83 Hz, 1H) 7.26 (s, 1H) 7.38-7.43 (m, 2H); $^{13}$C NMR (75 MHz, CDCl$_3$) δ 20.3, 28.0, 32.4, 36.3, 52.0, 52.4, 129.9, 130.5, 131.3, 131.9, 132.8, 136.1, 173.5; FT-IR (neat): 2950, 2843, 1718, 1474, 1247 cm$^{-1}$; HRMS (pos-APCI) calcd for $C_{13}H_{16}O_2NCl_2$: 288.05526 Found: 288.05516.

Methyl 1-(3,4-dichlorophenyl)-2-((methylamino) methyl)cyclopropanecarboxylate fumarate (5e salt)

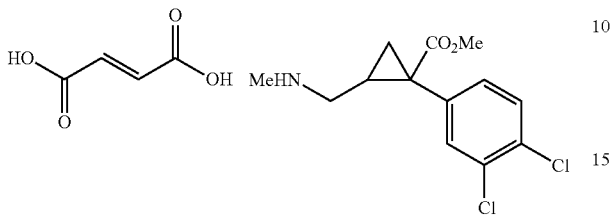

Methyl 1-(3,4-dichlorophenyl)-2-((methylamino)methyl) cyclopropanecarboxylate (288 mg, 1 mmol) was dissolved in isopropanol (20 mL) and then treated with fumaric acid (116 mg, 1 mmol) and stirred for 30 minutes at room temperature. The mixture was then concentrated under reduced pressure and the residue was re-dissolved in 2:1:1 isopropanol/hexanes/ethyl acetate (10 mL) and refluxed for 2 hours. The solution was cooled to room temperature and then to −20° C. using an acetone/ice bath. The resulting solid was filtered and washed with cold acetone to give off-white solid. $^1$H NMR (400 MHz, CD$_3$OD) δ 1.47-1.56 (m, 1H) 1.81 (dd, J=8.39, 5.03 Hz, 1H) 1.94-2.05 (m, 1H) 2.11-2.24 (m, 1H) 2.62 (s, 3H) 3.62 (s, 3H) 6.66 (s, 2H) 7.25 (dd, J=8.24, 1.83 Hz, 1H) 7.48-7.54 (m, 2H); $^{13}$C NMR (75 MHz, CD$_3$OD) δ 21.2, 23.8, 33.5, 33.5, 34.0, 50.9, 53.5, 131.7, 132.3, 133.2, 133.5, 134.4, 136.3, 136.7, 171.5, 174.1; FT-IR (neat): 3022, 2771, 1719, 1270 cm$^{-1}$; HRMS (pos-APCI) calcd for $C_{13}H_{16}O_2NCl_2$: 288.05526 Found: 288.05525.

Methyl 1-(2-chlorophenyl)-2-((methylamino) methyl)cyclopropanecarboxylate (5f)

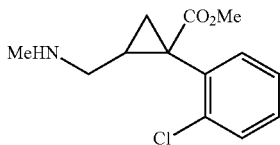 [SMILES: CNCC1CC1(C(=O)OC)c1ccccc1Cl]

In a 50 mL round bottom flask equipped with a magnetic stir bar, methyl 1-(2-chlorophenyl)-2-formylcyclopropanecarboxylate (238 mg, 1 mmol) was dissolved in methanol (20 mL) and flushed with argon. This solution was treated with methylamine (2M in MeOH, 0.5 mL, 2 mmol) and Ti(O-iPr)$_4$ (0.4 mL, 2 mmol) and stirred at room temperature for 16 hours. After the allotted time had passed, NaBH$_4$ (56 mg, 1.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 60% yield (152 mg). $^1$H NMR (400 MHz, CDCl$_3$) δ 1.28 (br. s., 1H) 1.41 (br. s., 1H) 1.59-1.86 (m, 2H) 2.34 (s, 3H) 2.74 (dd, J=12.36, 5.03 Hz, 1H) 3.59 (s, 3H) 7.20-7.31 (m, 2H) 7.35-7.40 (m, 1H); $^{13}$C NMR (75 MHz, CDCl$_3$) δ 20.6, 27.0, 32.2, 35.9, 50.8, 52.1, 126.4, 128.4, 129.1, 131.5, 134.4, 136.4, 173.2; FT-IR (neat): 2949, 1719, 1434, 1266, 1249, 728 cm$^{-1}$; HRMS (pos-APCI) calcd for $C_{13}H_{16}ClO2N$: 254.09423 Found: 254.09419.

Methyl 1-(2-chlorophenyl)-2-((methylamino) methyl)cyclopropanecarboxylate fumarate (5f salt)

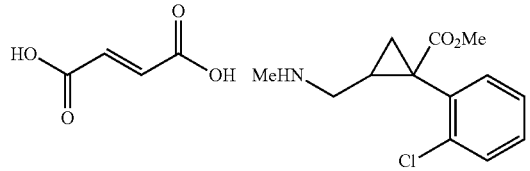 [SMILES: O=C(O)/C=C/C(=O)O ; CNCC1CC1(C(=O)OC)c1ccccc1Cl]

Methyl 1-(2-chlorophenyl)-2-((methylamino)methyl)cyclopropanecarboxylate (288 mg, 1 mmol) was dissolved in isopropanol (20 mL) and then treated with fumaric acid (116 mg, 1 mmol) and stirred for 30 minutes at room temperature. The mixture was then concentrated under reduced pressure and the residue was re-dissolved in 2:1:1 isopropanol/hexanes/ethyl acetate (10 mL) and refluxed for 2 hours. The solution was cooled to room temperature and then to −20° C. using an acetone/ice bath. The resulting solid was filtered and washed with cold acetone to give off-white solid. $^1$H NMR (400 MHz, CD$_3$OD) d 1.56-1.77 (m, 2H) 1.90 (br. s., 1H) 2.43 (br. s., 1H) 2.61 (s, 3H) 3.43 (d, J=10.37 Hz, 1H) 3.60 (s, 3H) 6.66 (s, 2H) 7.30-7.39 (m, 3H) 7.41-7.47 (m, 1H); $^{13}$C NMR (75 MHz, CD$_3$OD) δ 33.44, 33.47, 53.45, 128.74, 130.82, 130.98, 133.85, 134.64, 136.35, 171.56, 174.09

Methyl 1-(3,4-dimethoxyphenyl)-2-((methylamino) methyl)cyclopropanecarboxylate hydrochloride (5g salt)

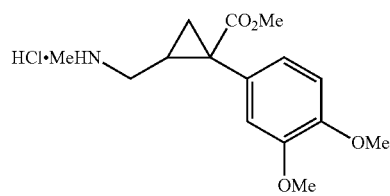

In a 50 mL round bottom flask equipped with a magnetic stir bar, crude mixture of methyl 1-(3,4-dimethoxyphenyl)-2-formylcyclopropanecarboxylate (264 mg, 1 mmol) was dissolved in methanol (20 mL) and flushed with argon. This solution was treated with methylamine (2M in MeOH, 0.5 mL, 2 mmol) and Ti(O-iPr)$_4$ (0.4 mL, 2 mmol) and stirred at room temperature for 16 hours. After the allotted time had passed, NaBH$_4$ (56 mg, 1.5 mmol) was added and the reaction was stirred for an additional 2 hours. The reaction was quenched with H$_2$O (1 mL) and filtered through a short path of celite and rinsed with diethyl ether. The organic filtrate was diluted with diethyl ether and washed with water, then brine, and dried over MgSO$_4$. The organic phase was then filtered and concentrated under reduced pressure and the resulting residue was purified by column chromatography (SiO$_2$, Isolera, ethyl acetate:triethylamine=9:1) to give colorless oil in 56% yield (156 mg) over two steps. The product was dissolved in diethyl ether (15 mL), then treated with hydrochloric acid in diethyl ether (2M in diethyl ether, 1 mL), and the resulting white solid was filtered and washed with diethyl ether to obtain white solid. $^1$H NMR (400 MHz, CDCl$_3$) δ 1.10 (t, J=5.03 Hz, 1H) 1.19 (br. s., 1H) 1.61 (dd, J=7.93, 3.97 Hz, 1H) 1.94 (d, J=7.93 Hz, 2H) 2.23 (s, 3H) 2.30-2.40 (m, 1H) 3.51 (s, 3H) 3.77 (d, J=1.83 Hz, 6H) 6.75 (d, J=16.48 Hz, 3H); $^{13}$C NMR (75 MHz, CDCl$_3$) δ 20.1, 27.7, 32.6, 36.1, 51.9, 51.9, 55.3, 55.5, 110.2, 113.9, 122.8, 127.9, 147.84, 148.0, 174.4; FT-IR (neat): 2950, 2837, 1715, 1516, 1249, 1226, 726 cm$^{-1}$; HRMS (pos-APCI) calcd for C$_{15}$H$_{22}$O$_4$N: 280.15433 Found: 280.15430.

(1R,2S)-methyl 1-phenyl-2-((E)-styryl)cyclopropan-ecarboxylate

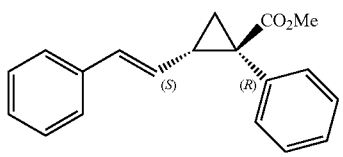

A solution of methyl 2-diazo-2-phenylacetate (250 mg, 1 mmol, and 1 eq.) in hexane (5 mL) was added by syringe pump over 1 hr to a solution of (E)-buta-1, 3-dienylbenzene (390.2 mg, 3 mmol, 3 eq.) and Rh$_2$ (S-DOSP)$_4$ (18 mg, 0.01 mmol, 0.1 eq.) in hexane (50 mL) at −45° C. The reaction mixture was stirred at −45° C. for an additional 2 h, and then concentrated in vacuo. Purified by flash chromatography on silica gel using 9:1 hexane/EtOAc as eluant to isolate colored oily liquid, 232 mg (83%). >94% de and 96% ee. $^1$H NMR (500 MHz, CDCl$_3$): δ7.25 (m, 5H), 7.12 (m, 2H), 7.05 (m, 3H), 6.52 (d, J=15.5 Hz, 1H), 5.18 (dd, J=15.5 Hz, 10.0 Hz, 1H), 3.52 (s, 3H), 2.66 (m, 1H) 2.02 (m, 1H), 1.42 (m, 1H). $^{13}$C NMR (300 MHz, CDCl$_3$): δ173.7 (C), 136.8 (C), 135.6 (C), 131.4 (CH), 131.0 (CH), 128.5 (CH), 128.1 (CH), 127.8 (CH), 127.0 (CH), 126.8 (CH), 125.6 (CH), 52.12 (CH$_3$), 35.47 (C), 31.65 (CH), 22.26 (CH$_2$). IR (CHCl$_3$): 1717, 1271, 1244, 1193, 1159, 960, 752, 694 cm$^{-1}$. HRMS (EI) m/z calcd for [C$_{19}$H$_{18}$O$_2$Na$_1$]$^+$ 301.1199. Found: 301.1194. [α]$^{20}_D$=−181° (10 mg/mL, MeOH). HPLC analysis: 96% ee (Chiralcel SS-Whelk, 1% i-PrOH in hexane, 0.6 ml/min, λ=254 nm, $t_R$=24.3 min, minor; $t_R$=33.5 min, major).

(1S,2R)-methyl 1-phenyl-2-((E)-styryl)cyclopropan-ecarboxylate

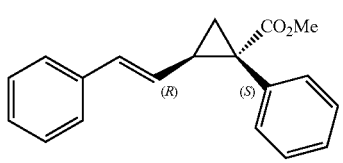

The enantiomer was made using Rh$_2$(R-DOSP)$_4$ as catalyst in the same reaction conditions as described above, to obtain the 256 mg (92%). >94% de and 92% ee. [α]$^{20}_D$=181° (10 mg/mL, MeOH). HPLC analysis: 96% ee (Chiralcel SS-Whelk, 1% i-PrOH in hexane, 0.6 ml/min, λ=254 nm, $t_R$=24.3 min, major; $t_R$=33.5 min, minor).

(1R,2R)-methyl 2-((methylamino)methyl)-1-phenyl-cyclopropanecarboxylate

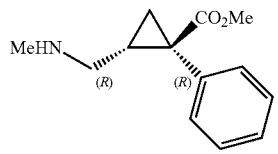

Ozone was bubbled through the solution of (E)-methyl 1-(phenyl)-2-styrylcyclopropanecarboxylate (556 mg, 2 mmol, 1 eq.) in DCM at −78° C. until blue color of ozone persists. The reaction mixture was stirred at −78° C. for an additional 2 h, and then PPh$_3$ was added. The crude mixture was concentrated in vacuo and dissolved in MeOH. Ti(O$^i$Pr)$_4$ and methylamine were added at RT and stirred for 2 hours. NaBH$_4$ was added in portions at RT. Bubbles were observed. The reaction mixture is quenched with H$_2$O, filtered through celite and extracted into EtOAc. The organic layer was dried over MgSO$_4$ and concentrated in vacuo to get crude mixture. The product was purified by flash chromatography on silica gel using 9:1 EtOAc/Et$_3$N as eluant to isolate colorless oily liquid, 271 mg (62% over 2 steps). $^1$H NMR (400 MHz, CDCl$_3$) δ 1.24 (dd, J=6.41, 4.58 Hz, 1H) 1.74 (dd, J=9.15, 4.27 Hz, 1H) 1.90-2.00 (m, 1H) 2.02-2.14 (m, 1H) 2.32 (s, 3H) 2.45 (dd, J=12.36, 5.95 Hz, 1H) 3.62 (s, 3H) 7.15-7.49 (m, 5H); $^{13}$C NMR (75 MHz, CDCl$_3$) δ 20.0, 27.7, 33.0, 36.1, 52.1, 127.0, 127.8, 130.85, 135.61, 174.35; FT-IR (neat): 2949, 2843, 1715, 1434, 1251, 700 cm$^{-1}$; HRMS (pos-APCI) calcd for C$_{13}$H$_{18}$O$_2$N: 220.13321. Found: 220.13306.

(1S,2S)-methyl 2-((methylamino)methyl)-1-phenyl-cyclopropanecarboxylate

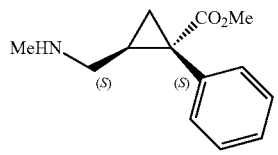

The enantiomer was made using the same reaction conditions as described above, to obtain product in 59% yield (258 mg) over 2 steps.

Figure 5:
FIG. 5 shows illustrative schemes for preparing compounds disclosed herein.
Figure 5:
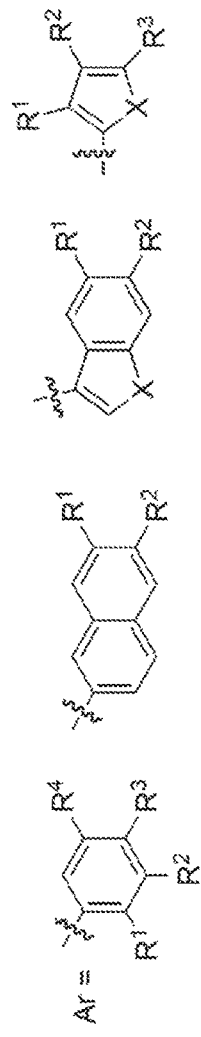
Figure 5:
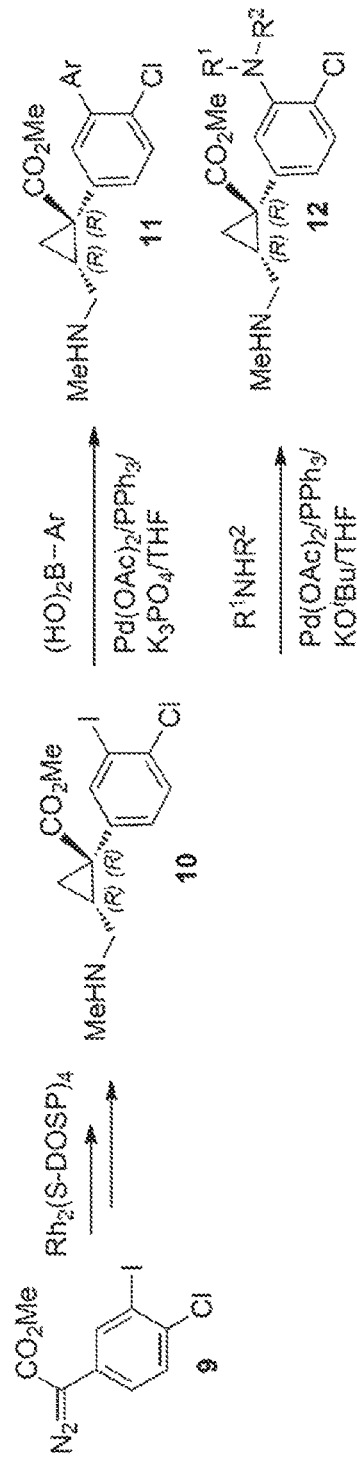

Modifying the procedures above with appropriate starting materials provides desired products in diastereomeric excess. For example, reductive amination described herein to make the N-methyl derivatives may be extended to a series of amines to generate a series of functionalized amines below. Other examples are illustrated in FIG. 5.

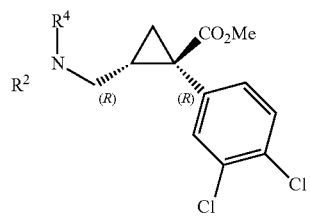

-continued $R^4NR^2 = NH_2, NMe_2, NEt_2$

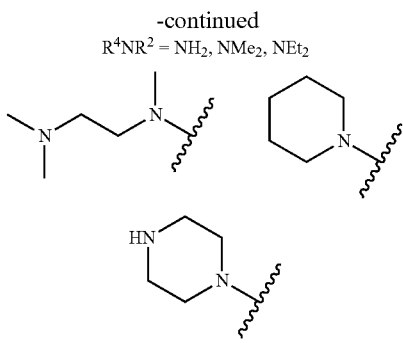

Transporter Binding Studies

Affinities of analogs at dopamine transport (DAT) sites are determined by displacement of [$^{125}$I]RTI-55 binding in membranes from rat striatum. See Boja et al., Eur. J. Pharmacol., 1991, 194, 133, hereby incorporated by reference. Frozen brains from Sprague-Dawley rats are obtained commercially and striata are dissected on ice. Tissue is homogenized in 10 vol of RTI-55 assay buffer (0.32 M sucrose, 10 mM sodium phosphate buffer, pH 7.4) with a Polytron, and centrifuged three times at 48,000g for 10 min, with fresh buffer resuspension for each centrifugation. Assay tubes contain 0.5 mg (original wet weight) of membranes, 0.01 nM [$^{125}$I]RTI-55, and various concentrations of unlabeled drugs dissolved in RTI-55 assay buffer in a final volume of 2 ml. Tubes are incubated for 50 min at 25° C., and the reaction is terminated by rapid filtration with 3-5 ml of cold Tris buffer through Whatman GF/B glass fiber filters pre-soaked in Tris buffer containing 0.1% BSA for at least 1 h. Non-specific binding is determined in the presence of 1 μMWF-23.

Affinities of analogs at 5-HT transport (SERT) sites are determined by displacement of [$^3$H] citalopram binding in membranes from rat frontal cortex. See D'Amato et al., J. Pharmacol. Exp. Ther., 1987, 242, 364 hereby incorporated by reference. Tissue is obtained from frozen rat brains as described above, homogenized in 10 vol of citalopram assay buffer (50 mM Tris-HCl, 120 mM NaCl, 5 mM KCl, pH 7.4) with a Polytron, and centrifuged two times at 48,000g for 10 min, with fresh buffer resuspension for each centrifugation. Assay tubes contain 50 mg (original wet weight) of membranes, 0.4 nM [$^3$H]citalopram, and various concentrations of unlabeled drugs dissolved in citalopram assay buffer in a final volume of 2 ml. Tubes are incubated for 60 min at 25° C., and the reaction is terminated by rapid filtration with 3×4 mL of cold Tris buffer through Whatman GF/B glass fiber filters pre-soaked in Tris buffer containing 0.1% BSA for at least 1 h. Non-specific binding is determined in the presence of 10 μM fluoxetine.

Binding of analogs at norepinephrine transporters (NET) was determined by displacement of [$^3$H]nisoxetine binding. See Tejani-Butt, J. Pharmacol. Exp. Ther., 1991, 260, 427, hereby incorporated by reference. Whole rat brains (minus cerebellum) are homogenized in 30 vol of 120 mM NaCl, 5 mM KCl, 50 mM Tris-HCl, pH 7.4, and centrifuged at 48,000g for 10 min. The membranes are resuspended in nisoxetine assay buffer (300 mM NaCl, 5 mM KCl, 50 mM Tris-HCl, pH 7.4) and centrifuged again before final resuspension in volumes of buffer. Assay tubes contain 750 μl of brain membranes, [$^3$H]nisoxetine (0.7 nM) together with unlabeled drugs dissolved in nisoxetine assay buffer to a final volume of 1 ml. Tubes are incubated for 40 min at 25° C., and the reaction is terminated by rapid filtration with 3×4 mL of cold Tris buffer through Whatman GF/B glass fiber filters which have been pre-soaked in Tris buffer containing 0.1% BSA for at least 1 h. Non-specific binding is determined in the presence of 1 μM desipramine. In [$^3$H]citalopram and [$^3$H]nisoxetine binding assays, radioactivity is determined by liquid scintillation spectrophotometry (efficiency: 50%) after eluting filters overnight in 5 mL of Ecolite scintillation fluid (ICN). IC$_{50}$ values are calculated from displacement curves using 7-10 concentrations of unlabeled analogs. Because binding of tropanes at dopamine transporter sites is generally regarded as multiphasic, potencies in inhibiting [$^{125}$I]RTI-55 binding are reported as IC$_{50}$ values. For [$^3$H]paroxetine and [$^3$H]nisoxetine binding assays, Ki values are calculated using the Cheng-Prusoff equation. See Cheng & Prusoff, Biochem. Pharmacol., 1973, 22, 3099 hereby incorporated by reference. In vitro data of cyclopropane amines is provided in Table 1.

TABLE 1

| Analog | Ar | Isomer | Log-P | NET | SERT | DAT |
|---|---|---|---|---|---|---|
| HD-283 | Milnacipran | (S,R) | 1.91 | 23.8 ± 1.7 | 35.1 ± 4.4 | 1970 ± 230 |
| HD-284 | C$_6$H$_5$ | ± | 1.65 | 152 ± 65 | 157 ± 4.8 | 1780 ± 87 |
| HD-285 | 4-BrC$_6$H$_4$ | ± | 2.51 | 3.7 ± 1.4 | 210 ± 10 | 1460 ± 470 |
| HD-286 | 4-PhC$_6$H$_4$ | ± | 3.54 | 315 ± 100 | 4.85 ± 1.0 | 189 ± 79 |
| HD-287 | 2-naphthyl | ± | 2.82 | 3.49 ± 0.64 | 6.58 ± 0.71 | 177 ± 44 |
| HD-288 | 3,4-diClC$_6$H$_3$ | ± | 2.95 | 0.80 ± 0.02 | 5.6 ± 0.39 | 107 ± 22 |
| HD-289 | 3,4-di(OMe)C$_6$H$_3$ | ± | 1.31 | 8.62 ± 0.71 | 106 ± 21 | 1364 ± 198 |
| HD-290 | 2-ClC$_6$H$_4$ | ± | 2.36 | 289 ± 24 | 329 ± 54 | 1840 ± 350 |
| HD-324 | 4-BrC$_6$H$_4$ | (S, S) | 2.51 | 44.9 ± 1.0 | 946 ± 71 | >10,000 |
| HD-325 | 4-BrC$_6$H$_4$ | (R, R) | 2.51 | 2.49 ± 0.07 | 47.0 ± 2.9 | 333 ± 79 |
| HD-326 | 3,4-diClC$_6$H$_3$ | (S, S) | 2.95 | 8.11 ± 0.80 | 40.5 ± 4.3 | 299 ± 97 |
| HD-327 | 3,4-diClC$_6$H$_3$ | (R, R) | 2.95 | 0.31 ± 0.01 | 2.42 ± 0.31 | 23.8 ± 3.6 |
| HD-328 | 3,4-diBrC$_6$H$_3$ | (S, S) | 3.17 | 4.57 ± 0.66 | 18.4 ± 2.5 | 87.9 ± 9.5 |
| HD-329 | 3,4-diBrC$_6$H$_3$ | (R, R) | 3.17 | 0.62 ± 0.12 | 1.71 ± 0.05 | 35.2 ± 4.6 |
| HD-330 | 2-naphthyl | (S, S) | 2.82 | 16.4 ± 0.52 | 27.0 ± 3.4 | 313 ± 55 |
| HD-331 | 2-naphthyl | (R, R) | 2.82 | 10.4 ± 0.89 | 15.0 ± 2.8 | 320 ± 51 |
| HD-332 | 4-PhC$_6$H$_4$ | (S, S) | 3.54 | >10,000 | 79.8 ± 21 | 917 ± 62 |
| HD-333 | 4-PhC$_6$H$_4$ | (R, R) | 3.54 | 86.6 ± 19 | 2.69 ± 0.62 | 86.7 ± 37 |

Analgesia Testing Methods:
Spinal Nerve Ligation

A 3 cm incision was made in the back using the iliac crests as a midpoint. An incision was then made in the underlying muscle, which was then separated by both sharp and blunt dissection to expose the left transverse process of the fifth lumbar vertebra. The transverse process was removed using bone microrongeurs, and the fifth lumbar nerve was exteriorized from underneath the spinal column using a small metal hook and ligated using 4.0 silk suture with sufficient pressure to cause the nerve to bulge on each side of the ligature. The sixth lumbar nerve was exteriorized from underneath the iliac bone at the sciatic notch and ligated in a similar manner. All muscle layers were sutured using 4.0 chromic gut, the skin was sutured using 4.0 nylon suture.

Intrathecal Catheter Implantation

The animal is placed in a stereotaxic frame to immobilize the head under pentobarbital anesthesia. The animal's body is lifted and supported to render the spinal column straight and level and the animal's head is placed downward such the top of the skull forms a 90° angle with the spinal column. A small incision is placed at the back of the neck and the underlying muscles are blunt dissected to reveal the atlanto-occipital membrane. A small incision is placed in the atlanto-occipital membrane through which a 32 ga polyethylene catheter is inserted that is 8 cm in length. The catheter is anchored to the neck muscles with 4.0 silk suture and the exterior wounds are closed with 4.0 nylon suture.

Drug Administration

All compounds were dissolved in 0.9% (wt/vol) saline, pH 7.4 and administered through the intrathecal catheter in a volume of 5 µl, followed by 15 µl of 0.9% saline to flush the catheter.

Determination of Mechanical Allodynia (Paw Withdrawal Threshold)

Paw withdrawal threshold was determined before and at selected time points following intrathecal drug administration using calibrated von Frey filaments. The animals are placed in elevated Plexiglas chambers with wire mesh floors and acclimated for a minimum of 30 minutes. Beginning with a filament calibrated to bend with a force of 2 g of pressure, the filament is applied to the plantar surface of the left hindpaw with sufficient force to bend slightly and left in place for 8 seconds or until the animal withdraws it's paw from the filament. In the absence of a paw withdrawal, the next highest calibrated filament is applied in a similar manner. In the presence of a paw withdrawal, the next lowest calibrated filament is applied. This up-down method continues until 4 responses are recorded after an initial positive response. The paw withdrawal threshold is calculated using Dixon non-parametric statistics.

Anti-Allodynic Effects of Novel SNRI Analogs

The potency and efficacy of novel SNRI analogs in reversing mechanical hypersensitivity were determined in the L5/L6 spinal nerve ligation (SNL) model of neuropathic pain in rats. Compounds were administered intrathecal (i.t.) and the effect on paw withdrawal threshold was assessed at various time points following treatment. The effects of HD-288 (NET selective), HD-283 (milnacipran, non-selective), and HD-286 (SERT selective) were determined and compared to those of clonidine, a drug approved for treatment of neuropathic pain in humans by spinal administration.

Figure 3:
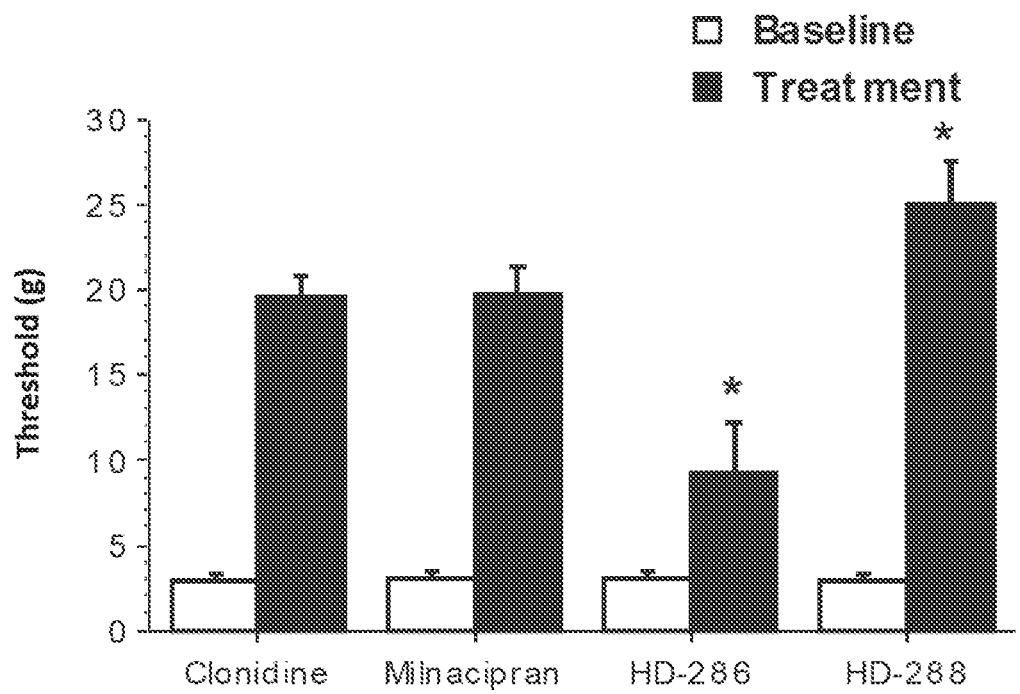
FIG. 3 shows data on the anti-allodynic effects of SNRI analogs and clonidine. All compounds were administered i.t. and paw withdrawal threshold was determined before (baseline) and following drug treatment (treatment) in a similar manner. Maximally effective doses were given for clonidine (10 μg), Milnacipran (30 μg), HD-286 (3 μg) and HD-288 (3 μg). N=8-10/group. *, significantly different from clonidine, p≤0.05.

HD-288 was potent following i.t. administration, producing significant anti-allodynic effects with an A50 of 0.6±0.3 µg and increasing the PWT from 2.9±0.4 g to 24.9±2.5 g at 3 µg. Clonidine (10 µg, i.t.) and HD-283 (milnacipran, 30 µg, i.t.) reversed mechanical allodynia in SNL rats similar to literature values. HD-286 produced an increase in PWT in SNL rats over a similar dose range as HD-288 with significantly lower efficacy, consistent with reports of the limited efficacy of SERT inhibitors against neuropathic pain (FIG. 3). The maximum effect of HD-288 was found to be significantly greater than clonidine. Therefore, HD-288 appears to be efficacious in reversing a symptom of neuropathic pain (mechanical allodynia) in nerve-injured rats and is quite potent compared to medications approved for clinical treatment of chronic pain (clonidine, milnacipran).

Figure 4:
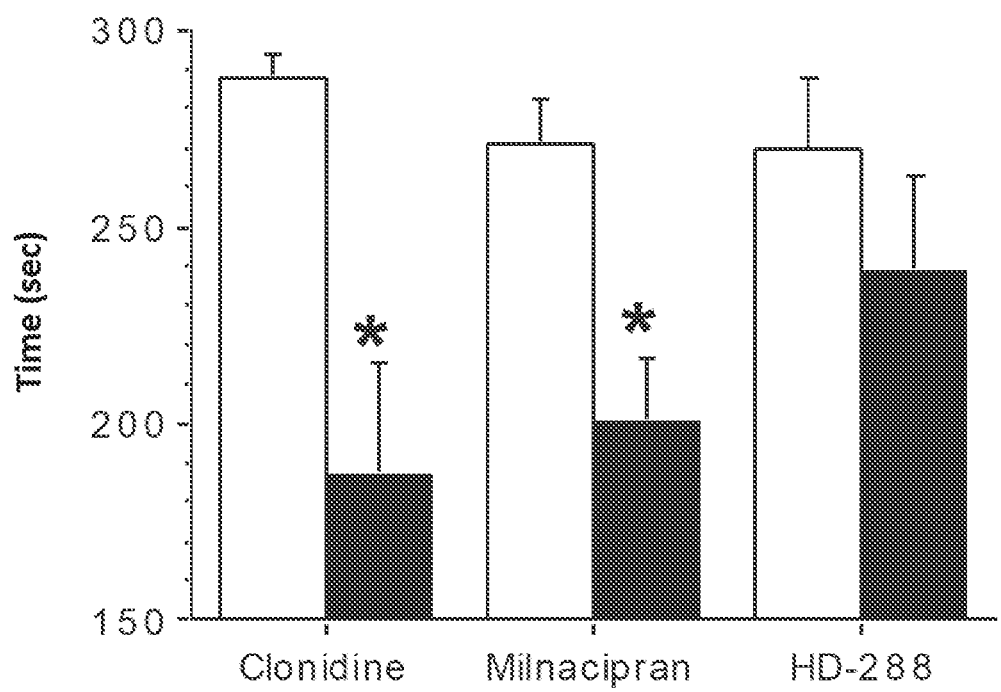
FIG. 4 shows data on the effects of clonidine, milnacipran and HD-288 on rotarod performance in SNL rats. Rats were trained to walk on a rotarod apparatus during 5 minute trials on two successive days. The rotarod was accelerated from 2 to 5 rpm over a 5 min period and the time until the rat fell from the rotarod was recorded. Each trial was a maximum of 5 min in duration. Shown are the mean±SEM for time spent on the rotarod before (baseline) or after (Treatment) drug administration (N=10-13 per group). * significantly different from Baseline, p≤0.05.

Effects of Novel SNRI Analogs on Sedation and/or Motor Coordination in the Rotarod Assay Rotarod performance was assessed to determine the relative potency of novel SNRI analogs as well as clonidine for producing sedation and/or motor impairment, two important dose-limiting side effects of these compounds. Clonidine (10 µg, i.t.) decreased the time rats were able to stay on the rotarod by 35±10% of baseline values [$F(1.25)=12.3$, $p=0.002$] (FIG. 4). Administration of the maximum dose of HD-288 (3 µg, i.t.) had no significant effect on rotarod performance [$F(1.19)=1.02$, $p=0.3$]. Sedation is a major dose-limiting side effect of clonidine and HD-288 appears to produce greater anti-allodynic effects and less sedation than clonidine in the rat.

The invention claimed is:

1. A composition comprising (1R,2R)-methyl 1-(3,4-dichlorophenyl)-2-((methylamino)methyl)cyclopropane carboxylate, or salts thereof.

2. The composition of claim 1, wherein the compound is in greater than 60% diastereomeric excess.

3. A pharmaceutical composition comprising a compound of claim 1 or pharmaceutically acceptable salt or prodrug thereof.

4. A pharmaceutical composition of claim 3 further comprising a second therapeutic agent.

* * * * *